United States Patent
Tone et al.

(10) Patent No.: US 12,024,526 B2
(45) Date of Patent: Jul. 2, 2024

(54) FUSED POLYCYCLIC AROMATIC COMPOUND

(71) Applicant: Nippon Kayaku Kabushiki Kaisha, Tokyo (JP)

(72) Inventors: Yusuke Tone, Tokyo (JP); Nozomi Onodera, Tokyo (JP); Hidenori Yakushiji, Tokyo (JP); Kazuki Niimi, Tokyo (JP); Satoshi Iwata, Tokyo (JP); Taku Iino, Tokyo (JP); Shunsuke Hori, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 348 days.

(21) Appl. No.: 17/642,808

(22) PCT Filed: Sep. 7, 2020

(86) PCT No.: PCT/JP2020/033726
§ 371 (c)(1),
(2) Date: Mar. 14, 2022

(87) PCT Pub. No.: WO2021/054161
PCT Pub. Date: Mar. 25, 2021

(65) Prior Publication Data
US 2023/0047095 A1 Feb. 16, 2023

(30) Foreign Application Priority Data

Sep. 17, 2019 (JP) .................................. 2019-168260
Dec. 5, 2019 (JP) .................................. 2019-220288
(Continued)

(51) Int. Cl.
*H01L 51/50* (2006.01)
*C07D 495/04* (2006.01)
(Continued)

(52) U.S. Cl.
CPC ....... *C07D 495/04* (2013.01); *H10K 85/6576* (2023.02); *H10K 10/462* (2023.02); *H10K 30/30* (2023.02)

(58) Field of Classification Search
CPC ... H10K 85/6576; H10K 10/462; H10K 30/30
See application file for complete search history.

(56) References Cited

U.S. PATENT DOCUMENTS

2010/0065826 A1  3/2010  Takimiya et al.
2011/0303910 A1  12/2011 Kuwabara et al.
(Continued)

FOREIGN PATENT DOCUMENTS

JP   2009196975 A   9/2009
JP   5404865 B2     2/2014
(Continued)

OTHER PUBLICATIONS

Sawamoto et al., "Soluble Dinaphtho[2,3-b:2',3'-f]thieno[3,2-b]thiophene Derivatives for Solution-Processed Organic Field-Effect Transistors", ACS Applied Materials & Interfaces, 2016, pp. 3810-3824, vol. 8, ACS Publications.

*Primary Examiner* — Anthony Ho
(74) *Attorney, Agent, or Firm* — The Webb Law Firm

(57) ABSTRACT

The present invention includes a fused polycyclic aromatic compound represented by general formula (1), where in formula (1), one among $R_1$ and $R_2$ is represented by general formula (2) and represents a substituent having three to five ring structures, and the other among $R_1$ and $R_2$ represents a hydrogen atom, where in formula (2), n represents an integer of 0-2, $R_3$ represents a divalent linking group obtained by removing two hydrogen atoms from benzene or naphthalene, $R_4$ represents a divalent linking group obtained by removing two hydrogen atoms from an aromatic ring of an aromatic hydrocarbon, and when n is 2, a plurality of $R_4$'s may be the same as or different from each other, $R_5$ represents an aromatic hydrocarbon group.

10 Claims, 11 Drawing Sheets

(30) Foreign Application Priority Data

| | | |
|---|---|---|
| Dec. 6, 2019 | (JP) | 2019-220873 |
| Dec. 26, 2019 | (JP) | 2019-236662 |
| Feb. 12, 2020 | (JP) | 2020-021192 |

(51) Int. Cl.
  *H10K 85/60* (2023.01)
  *H10K 10/46* (2023.01)
  *H10K 30/30* (2023.01)

(56) References Cited

U.S. PATENT DOCUMENTS

2013/0330876 A1  12/2013  Takimiya et al.
2014/0187792 A1  7/2014  Ikeda et al.

FOREIGN PATENT DOCUMENTS

| JP | 5674916 B2 | 2/2015 |
| JP | 5901732 B2 | 4/2016 |
| JP | 2018026559 A | 2/2018 |
| JP | 2018078270 A | 5/2018 |
| JP | 2018206878 A | 12/2018 |
| WO | 2008050726 A1 | 5/2008 |
| WO | 2010098372 A1 | 9/2010 |
| WO | 2014115749 A1 | 7/2014 |
| WO | 2016088793 A1 | 6/2016 |

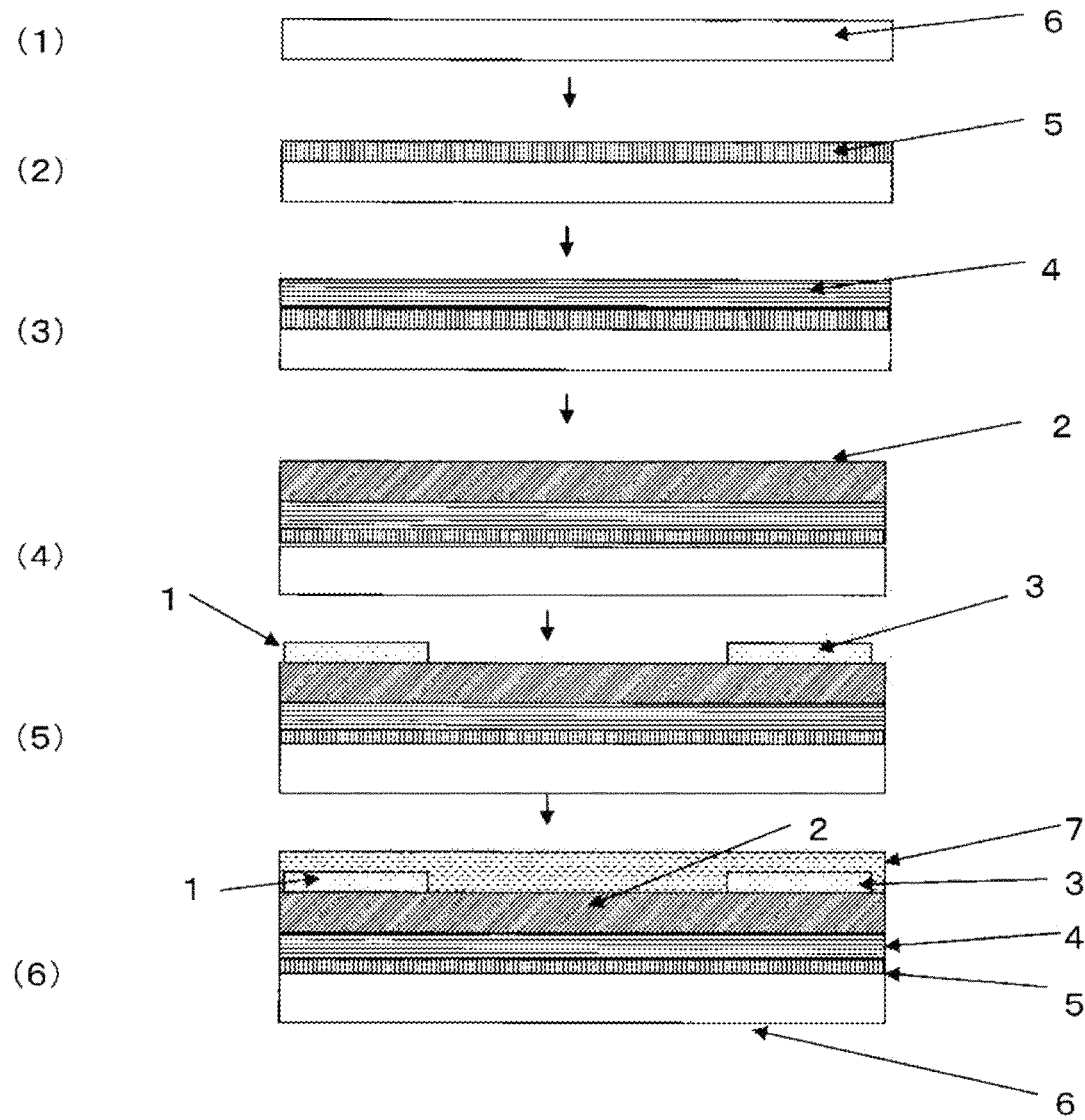
[Fig. 2]

[Fig. 3]
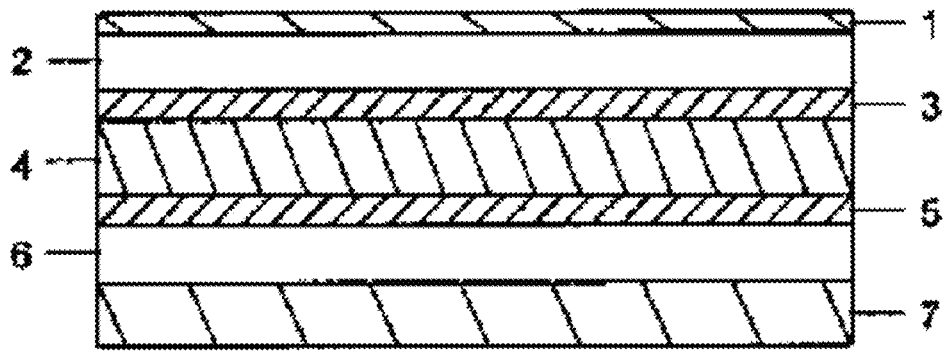

[Fig. 4]
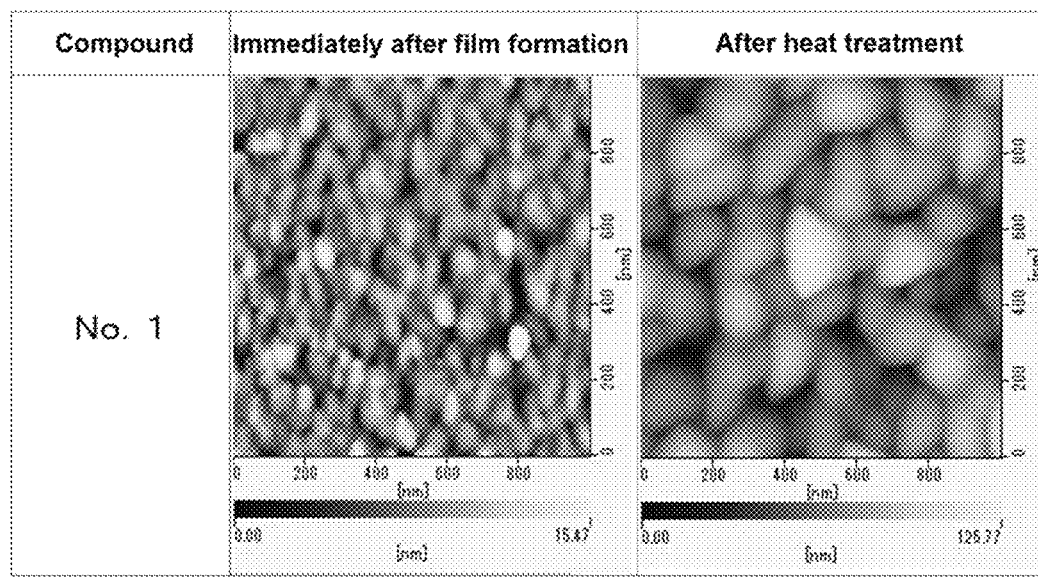

[Fig. 5]
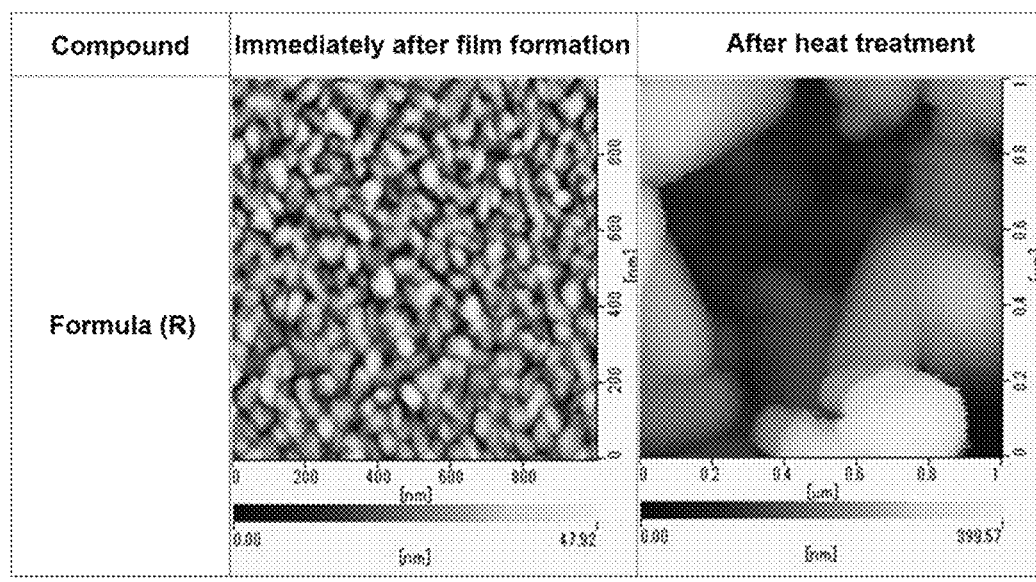

[Fig. 6]
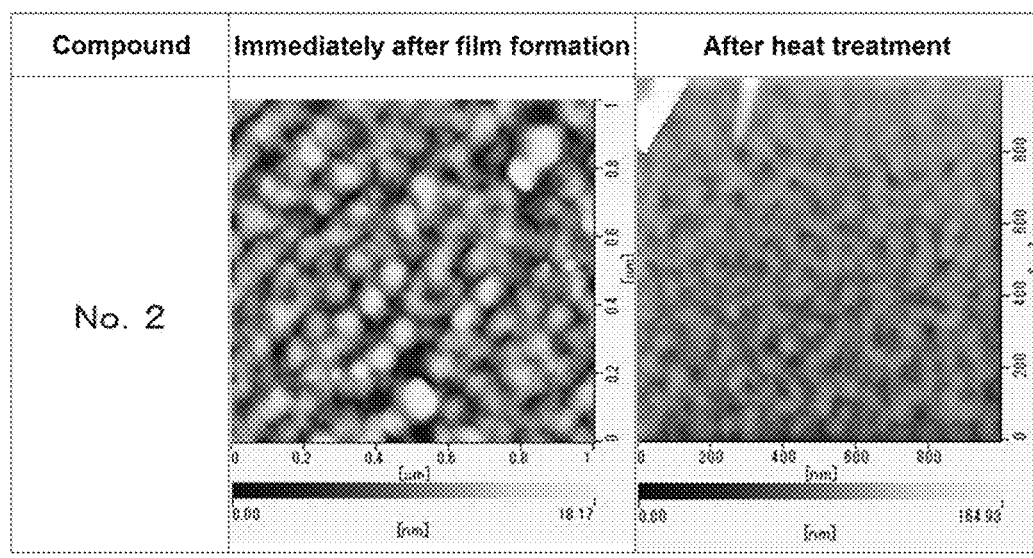

[Fig. 7]
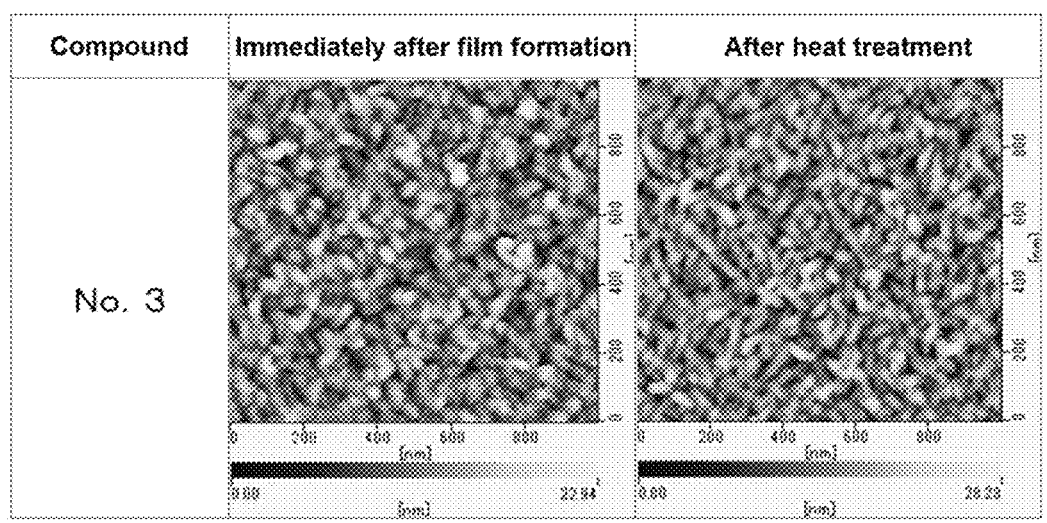

[Fig. 8]
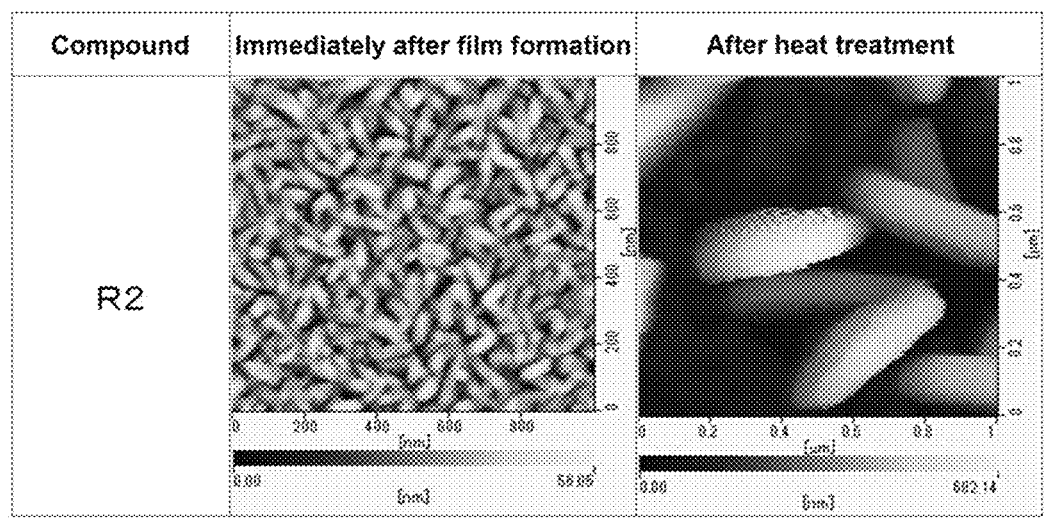

[Fig. 9]
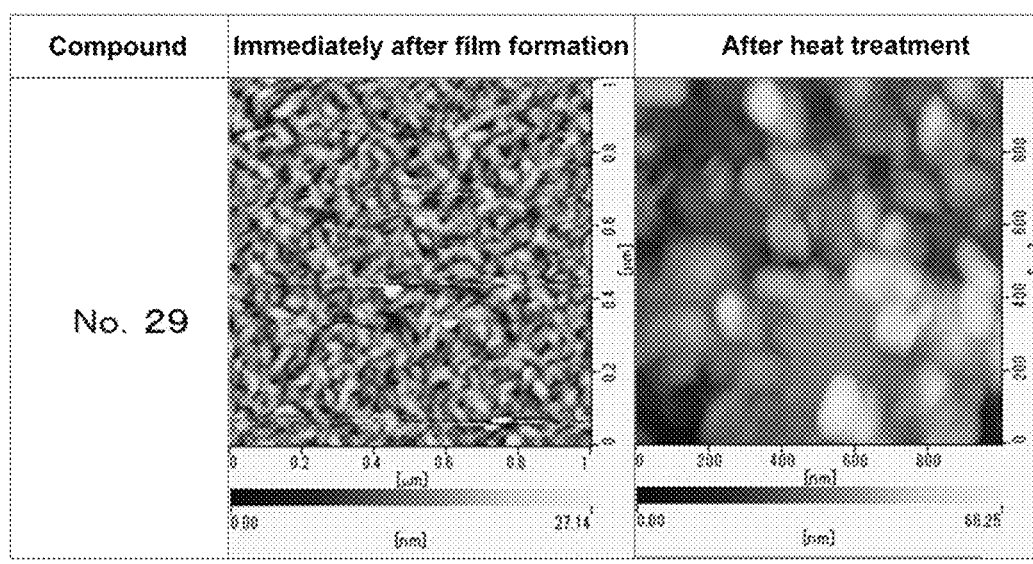

[Fig. 10]
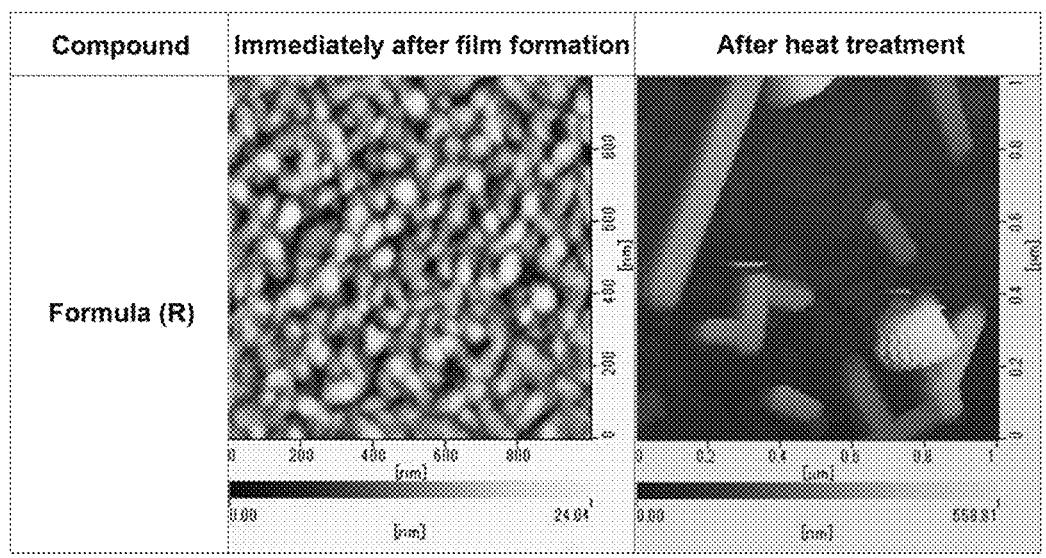

[Fig. 11]
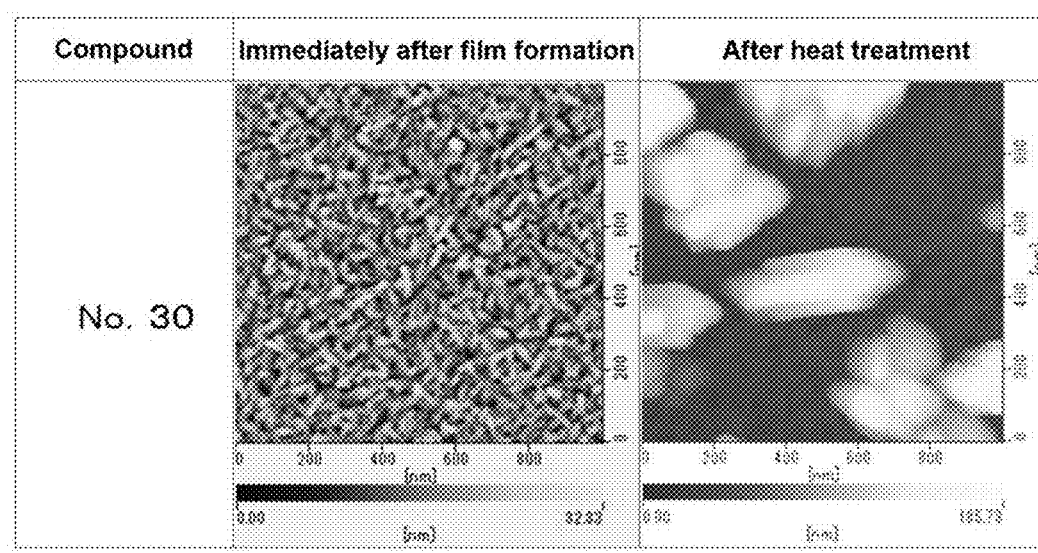

FUSED POLYCYCLIC AROMATIC COMPOUND

CROSS-REFERENCE TO RELATED APPLICATIONS

This application is the United States national phase of International Application No. PCT/JP2020/033726 filed Sep. 7, 2020, and claims priority to Japanese Patent Application Nos. 2019-168260 filed Sep. 17, 2019, 2019-220288 filed Dec. 5, 2019, 2019-220873 filed Dec. 6, 2019, 2019-236662 filed Dec. 26, 2019, and 2020-021192 filed Feb. 12, 2020, the disclosures of which are hereby incorporated by reference in their entirety.

BACKGROUND OF THE INVENTION

Field of the Invention

The present invention relates to a novel fused polycyclic aromatic compound and the use thereof. More specifically the present invention relates to a fused polycyclic aromatic compound that is dinaphtho[3,2-b:2',3'-f]thieno[3,2-b]thiophene (hereinafter abbreviated as "DNTT") derivative, an organic thin film containing said compound, and a field-effect transistor having said organic thin film.

Description of Related Art

Recently the organic thin film device such as the organic FET (field-effect transistor) device attracts attention. Various organic electronics materials represented by the fused polycyclic aromatic compound used for these thin film devices have been studied and developed.

For example, Patent Documents 1 and 2 disclose that the DNTT derivative shows excellent electric charge mobility and the thin film has organic semiconductor characteristics. However, because the DNTT derivatives disclosed in Patent Documents 1 and 2 have poor solubility in organic solvent and the organic semiconductor layer cannot be manufactured by the solution processes such as application method, and the organic thin film layer is formed by vapor deposition process.

But there is a problem that when the aromatic group having a large number of ring structures is substituted in the DNTT skeleton, the sublimation temperature of the DNTT derivative increases, as a result the thermal decomposition occurs in the vapor deposition process.

To this problem, Patent Document 3 and Non-Patent Document 1 show that the solubility in the organic solvent improves by introducing the branched chain alkyl group into the DNTT skeleton. Patent Document 4 discloses that the solubility of the DNTT skeleton improve by introducing the substituent into the aromatic ring adjacent to the central thiophene ring part and that the organic thin film device having the organic semiconductor layer manufactured by the solution process is obtained.

Thus, a DNTT derivative useful as an organic electronics compound has been developed so far. But there is a problem that the organic semiconductor characteristics of the thin film containing the DNTT derivatives in these documents decrease remarkably in the thermal annealing step after manufacturing the electrode of the field-effect transistor element.

In Patent Document 5 the application of the DNTT derivative for the photoelectric conversion element is examined. However, the method cited as the synthesis method of the DNTT derivative in the document and disclosed in Patent Document 6 and Patent Document 7 require that the DNTT derivative is synthesized after introducing the substituent into the 2-position or 3-position of the naphthalene skeleton in advance. Because the synthesis method of the DNTT derivative has low versatility and there is a problem in the suppression of the dark electric current generation in the low voltage region, the photoelectric conversion element having the large bright-dark electric current ratio in the lower voltage region is required.

CITATION LIST

Patent Document

Patent Document 1: WO 2008/050726 A
Patent Document 2: WO 2010/098372 A
Patent Document 3: WO 2014/115749 A
Patent Document 4: JP 5,404,865 B
Patent Document 5: JP 2018-26559 A
Patent Document 6: JP 5,674,916 B
Patent Document 7: JP 5,901,732 B

Non-Patent Document

Non-Patent Document 1: ACS Appl. Mater. Interfaces, 8, 3810-3824 (2016)

SUMMARY OF INVENTION

Technical Problem

The purpose of the present invention is to provide the fused polycyclic aromatic compound capable of introducing various substituents by the simple synthesis method, the organic thin film containing said compound, and the organic semiconductor device (the field-effect transistor having excellent heat resistance, the photoelectric conversion element having the large bright-dark electric current ratio in the low voltage region) having said organic thin film.

Solution to Problem

The previously-described problems may be solved by using a novel fused polycyclic aromatic compound having the specific structure so as to finish the present invention.

That is, the present invention relates to:

[1] A fused polycyclic aromatic compound represented by general formula (1):

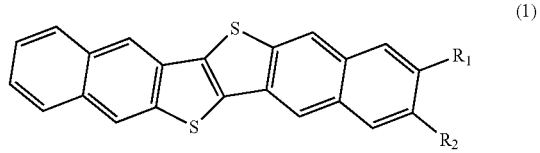

wherein in formula (1), one of $R_1$ and $R_2$ is represented by general formula (2) which is a substituent having 3 to 5 ring structures,

wherein in formula (2), n represents an integer of 0 to 2, $R_3$ represents a divalent linking group obtained by removing two hydrogen atoms from benzene or naphthalene, $R_4$ represents a divalent linking group obtained by removing two hydrogen atoms from an aromatic ring of an aromatic hydrocarbon, and when n is 2, a plurality of $R_4$s may be the same as or different from each other, $R_5$ represents an aromatic hydrocarbon group, and the other is a hydrogen atom.

[2] The fused polycyclic aromatic compound according to item [1], wherein the substituent represented by formula (2) has 21 to 30 carbon atoms.

[3] The fused polycyclic aromatic compound according to item [1] or [2] represented by general formula (3):

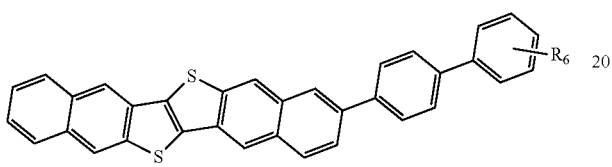
(3)

wherein in formula (3), $R_6$ is represented by general formula (4):

(4)

wherein in formula (4), m represents an integer of 0 or 1, $R_7$ represents a divalent linking group obtained by removing two hydrogen atoms from an aromatic ring of an aromatic hydrocarbon, and $R_8$ represents an aromatic hydrocarbon group.

[4] The fused polycyclic aromatic compound according to item [1], wherein the substituent represented by formula (2) is a phenyl group having an aromatic hydrocarbon group selected from a group consisting of phenylnaphthyl group, terphenyl group, biphenylnaphthyl group, phenanthrene group, anthranil group, naphthylphenyl group, fluorenyl group, and pyrenyl group.

[5] The fused polycyclic aromatic compound according to item [1] or [2] represented by general formula (5):

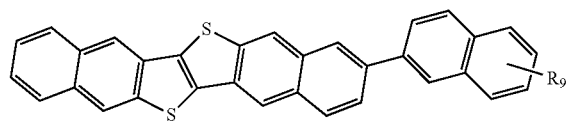
(5)

wherein in formula (5), $R_9$ is represented by general formula (6) which is a substituent having 1 to 3 ring structures:

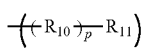
(6)

wherein in formula (6), p represents an integer of 0 to 2, $R_{10}$ represents a divalent linking group obtained by removing two hydrogen atoms from an aromatic ring of an aromatic hydrocarbon, Ru represents an aromatic hydrocarbon group.

[6] The fused polycyclic aromatic compound according to item [1], wherein the substituent represented by formula (2) is a naphthyl group having an aromatic hydrocarbon group selected from a group consisting of naphthyl group, biphenyl group, phenylnaphthyl group, terphenyl group, phenanthrene group, anthranil group, naphthylphenyl group, and fluorenyl group.

[7] An organic thin film containing the fused polycyclic aromatic compound according to any one of items [1] to [6].

[8] A field-effect transistor having the organic thin film according to item [7].

[9] A material for a photoelectric conversion element having the fused polycyclic aromatic compound according to any one of items [1] to [6].

[10] A photoelectric conversion element having the organic thin film according to item [7].

Effects of the Invention

The present invention can provide the fused polycyclic aromatic compound capable of introducing various substituents by the simple synthesis method and having excellent heat resistance in the practical process temperature, the organic thin film containing said compound, and the organic semiconductor device (field-effect transistor, organic photoelectric conversion element) having said organic thin film.

BRIEF DESCRIPTION OF DRAWINGS

FIG. 2 is the drawing illustrating the manufacturing steps for the top contact-bottom gate type field-effect transistor (element) as an embodiment of the field-effect transistor (element) of the present invention. The steps (1) to (6) are the schematic cross-sectional drawings showing each step.

FIG. 3 is the cross-sectional drawing showing the embodiment of the organic photoelectric conversion element of the present invention.

FIG. 4 is the AMF image of the organic thin film manufactured by using the fused polycyclic aromatic compound of the present invention.

FIG. 5 is the AMF image of the organic thin film manufactured by using the compound for comparison.

FIG. 6 is the AMF image of the organic thin film manufactured by using the fused polycyclic aromatic compound of the present invention.

FIG. 7 is the AMF image of the organic thin film manufactured by using the fused polycyclic aromatic compound of the present invention.

FIG. 8 is the AMF image of the organic thin film manufactured by using the compound for comparison.

FIG. 9 is the AMF image of the organic thin film manufactured by using the fused polycyclic aromatic compound of the present invention.

FIG. 10 is the AMF image of the organic thin film manufactured by using the compound for comparison.

FIG. 11 is the AMF image of the organic thin film manufactured by using the fused polycyclic aromatic compound of the present invention.

DESCRIPTION OF THE INVENTION

Figure 1A:
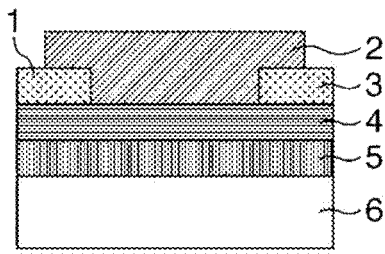
FIG. 1A is a schematic cross-sectional view of a bottom contact-bottom gate type field-effect transistor (element).

The present invention is described below in detail.

The fused polycyclic aromatic compound of the present invention is represented by general formula (1) aforementioned.

In general formula (1), one of $R_1$ and $R_2$ is represented by general formula (2) and represents a substituent having 3 to 5 ring structures, and the other represents a hydrogen atom.

Here, "the number of the ring structure in the substituent represented by general formula (2) having the ring structure" in the concrete examples described below of the fused polycyclic aromatic compound represented by general formula (1) is illustratively described. The compound of the concrete examples having 3 ring structures in the substituent represented by general formula (2) are No. 1 and No. 21. The compound of the concrete examples having 4 ring structures in the substituent represented by general formula (2) are Nos. 2, 3, 4, 11, 13, 16, 17, 18, 20, 22, 23, 24, 26, 27, 28, 29, 30, 36, 39, 41, 43, 49, 50, 51, 54, 55, 59, 60, and 61. The compound of the concrete examples having 5 ring structures in the substituent represented by general formula (2) are Nos. 5 to 10, 12, 14, 15, 19, 25, 31 to 35, 37, 38, 40, 42, 44 to 48, 52, 53, 56, 57, 58, 62, 63, and 64.

In general formula (2), n represents an integer of 0 to 2, $R_3$ represents a divalent linking group obtained by removing two hydrogen atoms from benzene or naphthalene, $R_4$ represents a divalent linking group obtained by removing two hydrogen atoms from an aromatic ring of an aromatic hydrocarbon, and when n is 2, a plurality of $R_4$s may be the same as or different from each other, $R_5$ represents an aromatic hydrocarbon group.

The aromatic hydrocarbon capable of being the divalent linking group represented by $R_4$ in general formula (2) is not limited as long as the compound has aromaticity, but the examples of the aromatic hydrocarbon include benzene, naphthalene, anthracene, phenanthrene, tetracene, chrysene, pyrene, triphenylene, fluorene, benzofluorene, acenaphthylene, and fluoranthene.

The divalent linking group represented by $R_4$ in general formula (2) is preferably the divalent linking group obtained by removing two hydrogen atoms from the aromatic ring of benzene, naphthalene, anthracene, phenanthrene or fluorene, more preferably the divalent linking group obtained by removing two hydrogen atoms from the aromatic ring of benzene or naphthalene.

The aromatic hydrocarbon group represented by $R_5$ in general formula (2) is meant to be a residue obtained by removing a hydrogen atom from the aromatic ring of the aromatic hydrocarbon.

The aromatic hydrocarbon capable of being the aromatic hydrocarbon group represented by $R_5$ in general formula (2) is not limited as long as the compound has aromaticity, but the examples of the aromatic hydrocarbon include benzene, naphthalene, anthracene, phenanthrene, tetracene, chrysene, pyrene, triphenylene, fluorene, benzofluorene, acenaphthylene, and fluoranthene.

The aromatic hydrocarbon group represented by $R_5$ in general formula (2) is preferably the aromatic hydrocarbon group obtained by removing a hydrogen atom from the aromatic ring of benzene, naphthalene, anthracene, phenanthrene, or fluorene, more preferably the aromatic hydrocarbon group obtained by removing a hydrogen atom from the aromatic ring of benzene or naphthalene.

The substituent represented by general formula (2) described above preferably contains 21 to 30 carbon atoms, more preferably 21 to 28 carbon atoms. "The number of carbon atoms contained in the substituent represented by general formula (2)" mentioned here is meant to be that when $R_3$ is phenylene group, the sum total of the number of carbon atoms in the phenylene group (namely 6), the number of carbon atoms in the divalent linking group $R_4$ (when there is a plurality of $R_4$, the sum of the number of carbon atoms in a plurality of $R_4$), and the number of carbon atoms of aromatic hydrocarbon group $R_5$. For example, "the number of carbon atoms in the substituent represented by general formula (2)" in the concrete example No. 1 described below of the fused polycyclic aromatic compound represented by general formula (1) is 6+6+6=18. "The number of carbon atoms in the substituent represented by formula (2)" in No. 15 is 6+10+10=26. When $R_3$ is naphthylene group, "the number of carbon atoms contained in the substituent represented by general formula (2)" is meant to be that the sum total of the number of carbon atoms in the naphthylene group (namely 10), the number of carbon atoms in the divalent linking group $R_4$ (when there is a plurality of $R_4$, the sum of the number of carbon atoms in a plurality of $R_4$), and the number of carbon atoms of aromatic hydrocarbon group $R_5$. For example, "the number of carbon atoms in the substituent represented by general formula (2)" in the concrete example No. 29 described below of the fused polycyclic aromatic compound represented by general formula (1) is 10+6+6=22. "The number of carbon atoms in the substituent represented by formula (2)" in No. 31 is 10+(6+6)+6=28. "The number of carbon atoms in the substituent represented by formula (2)" in No. 47 is 10+13=23. "The number of carbon atoms in the substituent represented by formula (2)" in No. 48 is 10+14=24.

In other embodiment of the present invention, the substituent represented by general formula (2) is preferably a phenyl group having an aromatic hydrocarbon group selected from a group consisting of phenylnaphthyl group, terphenyl group, biphenylnaphthyl group, phenanthrene group, anthranil group, naphthylphenyl group, fluorenyl group, and pyrenyl group, or a naphthyl group having an aromatic hydrocarbon group selected from a group consisting of naphthyl group, biphenyl group, phenylnaphthyl group, terphenyl group, phenanthrene group, anthranil group, naphthylphenyl group, and fluorenyl group.

The fused polycyclic aromatic compound represented by general formula (1) is preferably a compound wherein $R_1$ is the substituent represented by general formula (2) and $R_2$ is hydrogen atom. The substituent represented by general formula (2) is preferably the substituent wherein $R_3$ is phenylene group, n is 1 or 2, and $R_4$ bonding to $R_3$ is p-phenylene group, or the substituent wherein $R_3$ is naphthylene group and n is 0 or 1. Namely, the fused polycyclic aromatic compound represented by general formula (1) is more preferably the compound represented by general formula (3) or general formula (5) described above.

In general formula (3), $R_6$ represents the substituent represented by above general formula (4) and containing 9 to 18 carbon atoms and is preferably the substituent represented by general formula (4) and containing 9 to 16 carbon atoms. In general formula (4), m represents an integer of 0 or 1. $R_7$ represents the divalent linking group obtained by removing two hydrogen atoms from the aromatic ring of the aromatic hydrocarbon. $R_8$ represents the aromatic hydrocarbon group. Note that the phenylene group bonding to the BTBT skeleton in general formula (3) corresponds to $R_3$ in general formula (2), that the phenylene group bonding to the substituent represented by $R_6$ in general formula (3) corresponds to $R_4$ in general formula (2), and that the substituent represented by $R_6$ corresponds to $R_5$ when n is 1, or the part constituted of one of $R_4$s and $R_5$ when n is 2 in general formula (2).

Examples of the aromatic hydrocarbon capable of being the divalent linking group represented by $R_7$ in general formula (4) include the same as the aromatic hydrocarbon group capable of being the divalent linking group represented by $R_4$ in general formula (2). Examples of the preferable divalent linking group represented by $R_7$ include the same as the preferable divalent linking group represented by $R_4$.

Examples of the aromatic hydrocarbon capable of being the aromatic hydrocarbon group represented by $R_8$ in general formula (4) include the same as the aromatic hydrocarbon group capable of being the aromatic hydrocarbon group represented by $R_5$ in general formula (2). Examples of the preferable aromatic hydrocarbon group represented by $R_8$ is the same as the preferable aromatic hydrocarbon group represented by $R_5$.

"The number of carbon atoms contained in the substituent represented by general formula (4)" mentioned here is meant to be the total of the number of carbon atoms in the divalent group $R_7$ and the number of carbon atoms of aromatic hydrocarbon group $R_8$ in general formula (4).

In general formula (5), $R_9$ represents the substituent represented by general formula (6) and containing 1 to 3 ring structures and is preferably the substituent represented by general formula (6) and containing 11 to 20 carbon atoms. In general formula (6), p represents an integer of 0 to 2 and is preferably an integer of 0 or 1. $R_{10}$ represents the divalent linking group obtained by removing two hydrogen atoms from the aromatic ring of the aromatic hydrocarbon. $R_{11}$ represents the aromatic hydrocarbon group. Note that the naphthylene group bonding to the BTBT skeleton in general formula (5) corresponds to $R_3$ in general formula (2) and the substituent represented by $R_9$ in general formula (5) corresponds to the part constituted of $R_4$ and $R_5$ (when n is 1 or 2) or only $R_5$ (when n is 0) in general formula (2).

Examples of the aromatic hydrocarbon capable of being the divalent linking group represented by $R_{10}$ in general formula (6) include the same as the aromatic hydrocarbon group capable of being the divalent linking group represented by $R_4$ in general formula (2). Examples of the preferable divalent linking group represented by $R_{10}$ include the same as the preferable divalent linking group represented by $R_4$.

Examples of the aromatic hydrocarbon capable of being the aromatic hydrocarbon group represented by $R_{11}$ in general formula (6) include the same as the aromatic hydrocarbon group capable of being the aromatic hydrocarbon group represented by $R_5$ in general formula (2). Examples of the preferable aromatic hydrocarbon group represented by $R_{11}$ include the same as the preferable aromatic hydrocarbon group represented by $R_5$.

"The number of carbon atoms contained in the substituent represented by general formula (6)" mentioned here is meant to be the sum total of the number of carbon atoms in the divalent group $R_{10}$ and the number of carbon atoms of aromatic hydrocarbon group $R_{11}$ in general formula (6).

Next, the synthesis method of the fused polycyclic aromatic compound represented by general formula (1) of the present invention is described in detail. The fused polycyclic aromatic compound represented by general formula (1) can be synthesized by various well-known conventional methods. As one example, the synthesis method of the scheme where the compound (A) and the compound (B) are used as the starting materials, which is described below, is explained.

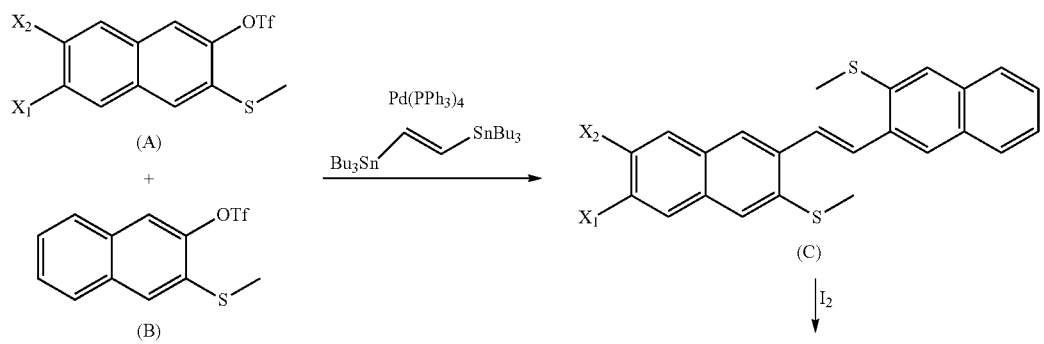

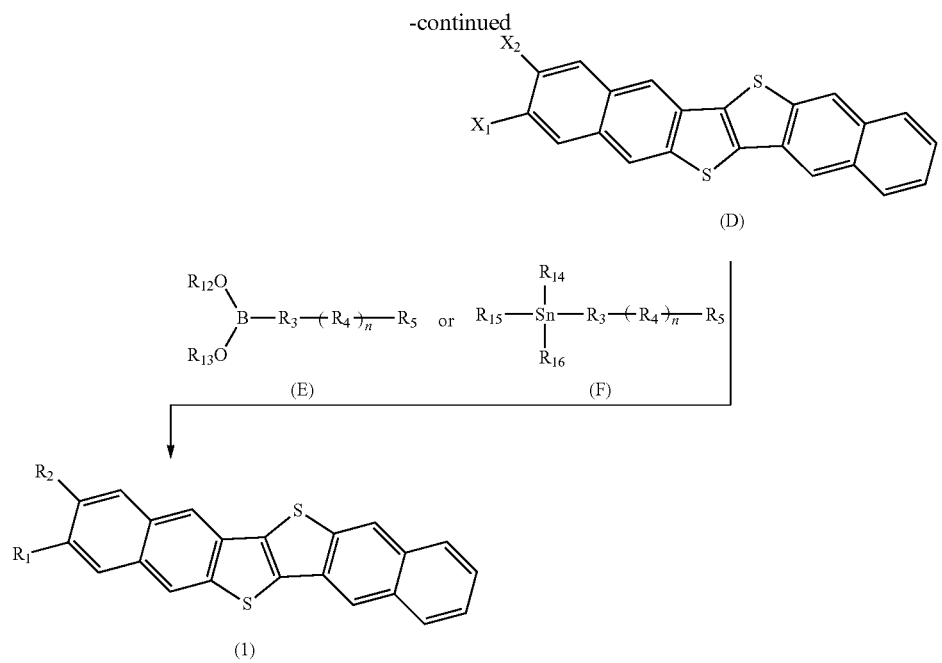

First, as a raw material, the compound (A) and the compound (B) are used to synthesize the compound (D) through the compound (C) by the method disclosed in JP2009-196975 A.

Next, the fused polycyclic aromatic compound represented by general formula (1) of the present invention is synthesized by using the compound (D) obtained above and the compound (E) or the compound (F) as a raw material. Here the reaction of the compound (D) and the compound (E) can be carried out by the well-known method equivalent to Suzuki-Miyaura coupling reaction and the reaction of the compound (D) and the compound (F) can be carried out by the well-known method equivalent to Migita-Kosugi-Stille cross-coupling method. For the details of these coupling reaction the description in for example "Metal-Catalyzed Cross-Coupling Reaction-Second, Completely Revised and Enlarged Edition" and the like can be referred to.

According to the above scheme, when the compound wherein $R_3$ is naphthylene (the divalent linking group obtained by removing two hydrogen atoms from naphthalene) is synthesized, it is not necessary that the DNTT derivative is synthesized after introducing the desired substituent into the 2-position or 3-position of the naphthalene skeleton in advance. After the DNTT skeleton is built, the substituent can be introduced by the cross-coupling reaction method. Therefore, the above scheme has high versatility, which is excellent.

In the above coupling reaction, the compound (E) or the compound (F) of 1 to 10 mol on basis of 1 mol of the compound (D) is preferably used, the compound (E) or the compound (F) of 1 to 3 mol is more preferably used.

The reaction temperature of the above coupling reaction is generally −10 to 200° C., preferably 40 to 160° C., more preferably 60 to 120° C. The reaction time is not particularly limited, but generally 1 to 72 hours, preferably 3 to 48 hours. Depending on the kind of the catalyst described below, the reaction temperature can be lowered, and the reaction time can be shortened.

The above coupling reaction is preferably carried out under the inert gas atmosphere such as argon atmosphere, nitrogen substitution, dry argon atmosphere, and dry nitrogen stream.

The catalyst is preferably used for the coupling reaction using the compound (E). Examples of the catalyst capable of using for the coupling reaction includes tri-tert-butyl phosphine, tri-adamanthyl phosphine, 1,3-bis(2,4,6-trimethyl phenyl)imidazoridinium chloride, 1,3-bis(2,6-diisopropylphenyl)imidazoridinium chloride, 1.3-diadamanthyl imidazoridinium chloride, or the mixture thereof; metal Pd, Pd/C (including water or not), palladium acetate, palladium trifluoro acetate, palladium methane sulphonate, palladium toluene sulphonate, palladium chloride, palladium bromide, palladium iodide, bis(acetonitrile)palladium(II) dichloride, bis(benzonitrile)palladium(II) dichloride, tetrakis(acetonitrile)palladium(II) tetrafluoroborate, tris(dibenzylidene acetone)dipalladium(0), tris(dibenzylidene acetone) dipalladium(0) chloroform complex, and bis(dibenzylidene acetone) palladium(0), bis(triphenylphosphino)palladium dichloride (Pd(PPh$_3$)$_2$Cl$_2$), (1,1'-bis(diphenylphosphino)ferrocene)palladium dichloride (Pd(dppf)Cl$_2$), tetrakis(triphenylphosphine)palladium (Pd(PPh$_3$)$_4$). The catalyst is preferably palladium based catalyst, more preferably Pd(dppf)Cl$_2$, Pd(PPh$_3$)$_2$Cl$_2$, Pd(PPh$_3$)$_4$, further preferably Pd(PPh$_3$)$_2$Cl$_2$, Pd(PPh$_3$)$_4$.

These catalysts may be used in mixture of two or more of or in mixture of the above catalyst with the other catalyst except for the above catalysts.

The amount of these catalysts used in the coupling reaction is preferably 0.001 to 0.500 mol, more preferably 0.001 to 0.100 mol, further preferably 0.001 to 0.050 mol based on 1 mol of the compound (E).

The basic compound is preferably used for the coupling reaction using the compound (E). Examples of the basic compound include hydroxides such as lithium hydroxide, barium hydroxide, sodium hydroxide, and potassium hydroxide, carbonates such as lithium carbonate, lithium hydrogen-carbonate, sodium carbonate, sodium hydrogen-carbonate, potassium carbonate, potassium hydrogen-carbonate, and cesium carbonate, acetates such as lithium acetate, sodium acetate, and potassium acetate, phosphates such as trisodium phosphate and tripotassium phosphate, alkoxides such as sodium methoxide, sodium ethoxide, and potassium tertiary butoxide; metal hydrides such as sodium hydride and potassium hydride, organic bases such as pyridine, picoline, lutidine, triethylamine, tributylamine, diisopropylethylamine, and N,N-dicyclohexylmethylamine. The basic compound is preferably phosphate or hydroxide, more preferably trisodium phosphate, tripotassium phosphate, sodium hydroxide, or potassium hydroxide. These basic compounds may be used alone or in combination of two or more.

The amount of these basic compounds used in the coupling reaction is preferably 1 to 100 mol, more preferably 1 to 10 mol, based on 1 mol of the compound (D).

The Pd based or the Ni based catalyst is preferably used for the coupling reaction using the compound (F). The catalyst can be used limitlessly as long as it is the Pd based or the Ni based catalyst. Examples of the Pd based catalyst includes the same catalysts as the catalysts described in the paragraph of the catalysts used for the coupling reaction using the compound (E).

Examples of the Ni based catalyst includes tetrakis(triphenylphosphine)nickel (Ni(PPh$_3$)$_4$), nickel(II)acetylacetonate (Ni(acac)$_2$), dichloro(2,2'-bipyridine)nickel (Ni(bpy)Cl$_2$), dibromobis(triphenylphosphine)nickel (Ni(PPh$_3$)$_2$Br$_2$), bis(diphenylphosphino)propanenickeldichloride (Ni(dppp)Cl$_2$), and bis(diphenylphosphino)ethanenickeldichloride (Ni(dppe)Cl$_2$). The Ni based catalyst is preferably Pd(dppf)Cl$_2$, Pd(PPh$_3$)$_2$Cl$_2$, Pd(PPh$_3$)$_4$, further preferably Pd(PPh$_3$)$_2$Cl$_2$, Pd(PPh$_3$)$_4$.

These catalysts may be used in mixture of two or more of or in mixture of the above catalyst with the other catalyst except for the above catalysts.

The amount of these catalyst used in the coupling reaction is preferably 0.001 to 0.500 mol, more preferably 0.001 to 0.100 mol, further preferably 0.001 to 0.050 mol based on 1 mol of the compound (F).

The alkali metal chloride may be used together in the coupling reaction using the compound (F).

The alkali metal chloride used together is not particularly limited as long as it is the salt containing the alkali metal, but the examples include lithium chloride, lithium bromide and lithium iodide. Lithium chloride is preferable.

The amount of the alkali metal chloride added is preferably 0.001 to 5.0 mol based on 1 mol of the compound (D).

The above coupling reaction can be carried out in the solvent. Any solvent can be used as long as the solvent can solve the compound (D), and the compound (E) or the compound (F) which are necessary raw materials, furthermore the catalyst, the basic compound, the alkali metal chloride, and the like which are used if necessary.

Examples of the solvent includes aromatic compounds such as chlorobenzene, o-dichlorobenzene, bromobenzene, nitrobenzene, toluene, xylene, saturated aliphatic hydrocarbons such as n-hexane, n-heptane, and n-pentane, alicyclic hydrocarbons such as cyclohexane, cycloheptane, and cyclopentane, saturated aliphatic halogenated hydrocarbons such as n-propylbromide, n-butylchloride, n-butylbromide, dichloromethane, dibromomethane, dichloropropane, dibromopropane, dichlorobutane, chloroform, bromoform, carbon tetrachloride, carbon tetrabromide, trichloroethane, tetrachloroethane, and pentachloroethane, halogenated cyclic hydrocarbons such as chlorocyclohexane, chlorocyclopentane, and bromocyclopentane, esters such as ethyl acetate, propyl acetate, butyl acetate, methyl propionate, ethyl propionate, propyl propionate, butyl propionate, methyl butyrate, ethyl butyrate, propyl butyrate, and butyl butyrate, ketones such as acetone, methylethylketone, and methylisobutylketone, ethers such as diethylether, dipropylether, dibutylether, cyclopentylmethylether, dimethoxyethane, tetrahydrofuran, 1,4-dioxane, and 1,3-dioxane; amides such as N-methyl-2-pyrolidone, N,N-dimethylformamide, and N,N-dimethylacetoamide, glycol such as ethyleneglycol, propyleneglycol, and polyethyleneglycol, and sulfoxides such as dimethylsulfoxide. These solvents may be used alone or in mixture of two or more.

The purification method for the fused polycyclic aromatic compound represented by general formula (1) is not particularly limited, but the well-known methods such as recrystallization, column chromatography, and vacuum sublimation purification can be used. These methods can be combined as necessary.

In the above synthesis scheme, one of $X_1$ and $X_2$ in the compounds (A), (C), and (D) represents iodine atom, bromine atom, or chlorine atom, preferably bromine atom, and the other represents hydrogen atom.

In the above synthesis scheme, $R_{12}$ and $R_{13}$ in the compound (E) each independently represent hydrogen atom or alkyl group, or combine with each other to form an alkylene group.

Example of the alkyl group represented by $R_{12}$ and $R_{13}$ includes the alkyl groups having a carbon number of 1 to 6 such as methyl group, ethyl group, n-propyl group, iso-propyl group, n-butyl group, sec-butyl group, iso-butyl group, tert-butyl group, n-pentyl group, and n-hexyl group.

Examples of the alkylene group formed by combining $R_{12}$ with $R_{13}$ include methylene group, ethane-1,2-diyl group, butane-2,3-diyl group, 2,3-dimethylbutane-2,3-diyl group, and propane-1,3-diyl group.

$R_{12}$ and $R_{13}$ in the compound (E) are preferably both hydrogen atoms or preferably combine with each other to form 2,3-dimethylbutane-2,3-diyl group.

In the above synthesis scheme, $R_{14}$ to $R_{16}$ in the compound (F) each independently represent linear or branched alkyl group. The carbon number of the alkyl group represented by $R_{14}$ to $R_{16}$ is generally 1 to 8, preferably 1 to 4. Examples of linear alkyl group include methyl group, ethyl group, n-propyl group, n-butyl group, iso-butyl group, n-pentyl group, and n-hexyl group. Examples of branched alkyl group include iso-propyl group, iso-butyl group, sec-butyl group, tert-butyl group, iso-pentyl group, and iso-hexyl group.

$R_{14}$ to $R_{16}$ in the compound (F) are preferably each independently methyl group or butyl group, and more preferably, all are methyl group or all are butyl group.

Note that $R_3$ to $R_5$ in the compounds (E) and (F) are synonymous with $R_3$ to $R_5$ in general formula (2).

The concrete examples of the fused polycyclic aromatic compound represented by general formula (1) are described below, but the present invention is not limited to these concrete examples.

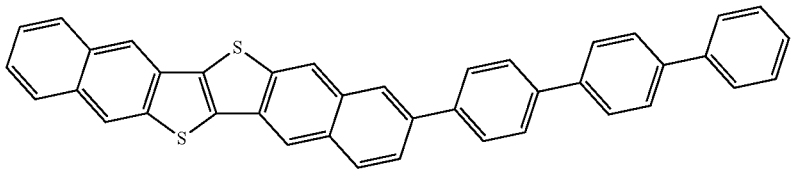
No. 1
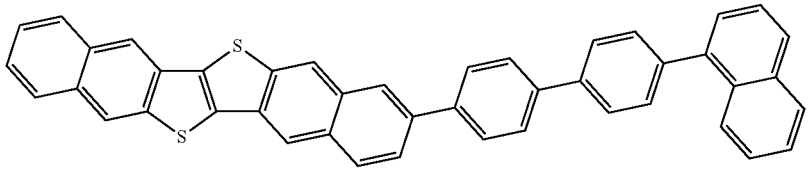
No. 2
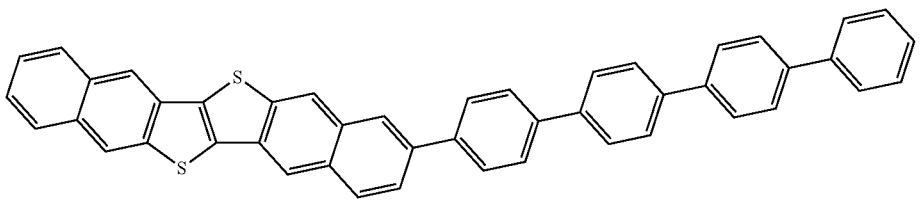
No. 3
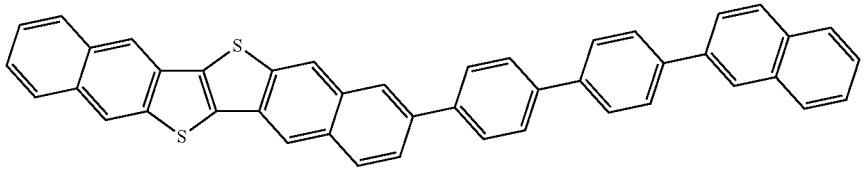
No. 4
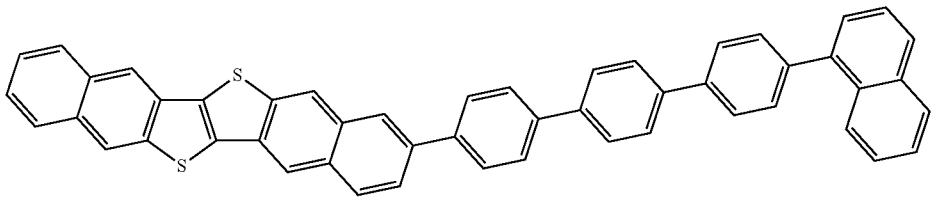
No. 5
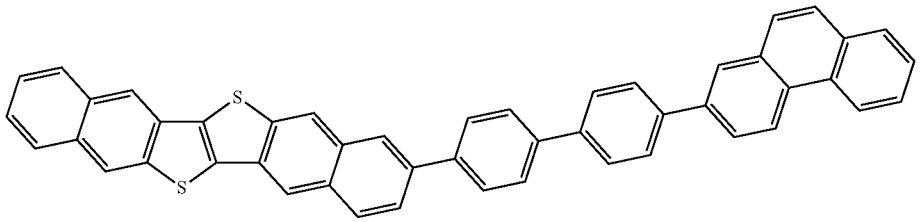
No. 6
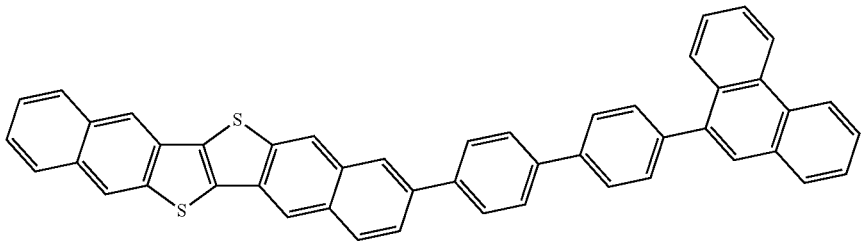
No. 7

-continued
No. 8
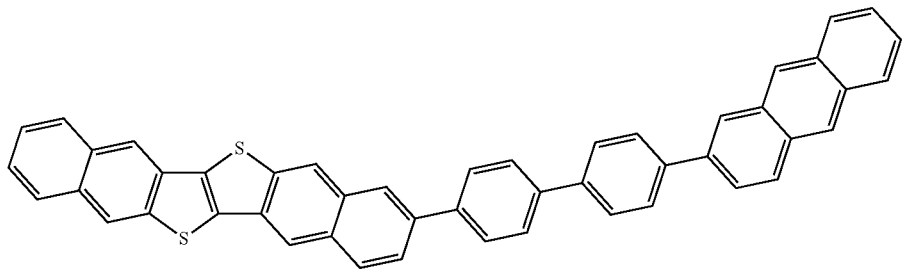
No. 9
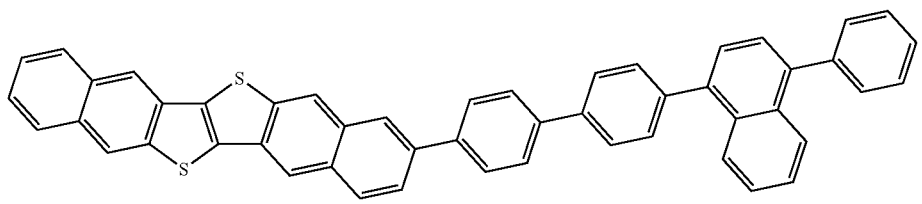
No. 10
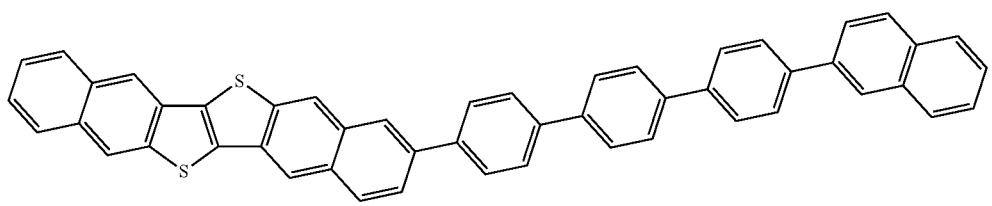
No. 11
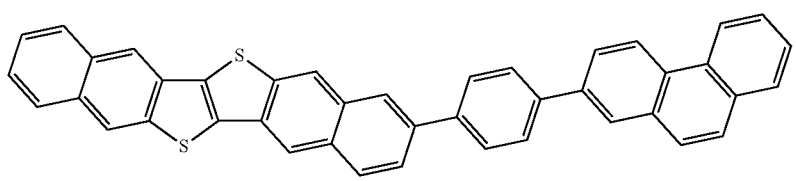
No. 12
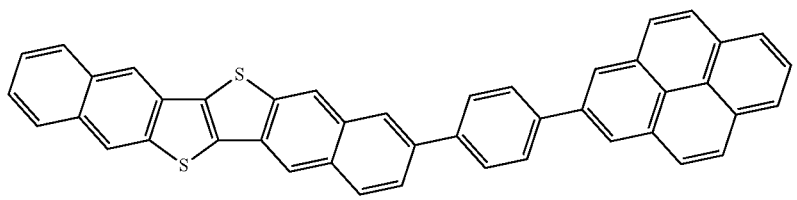
No. 13
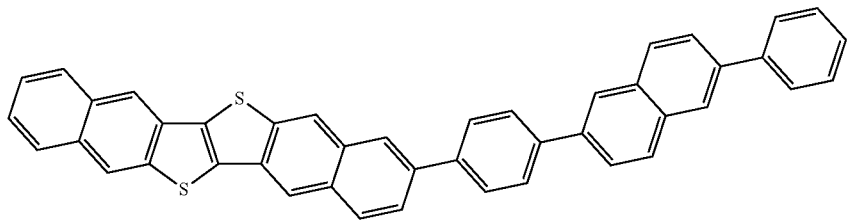
No. 14
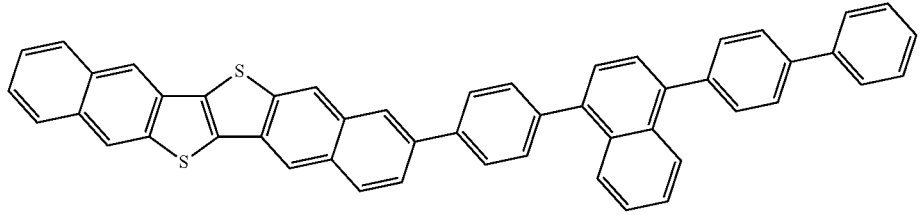

-continued
No. 15
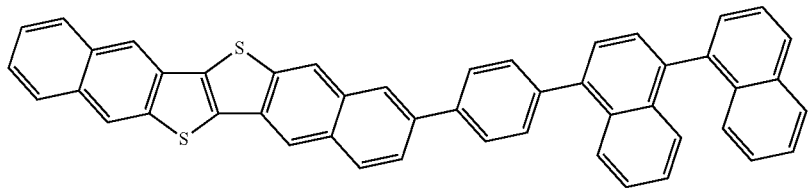
No. 16
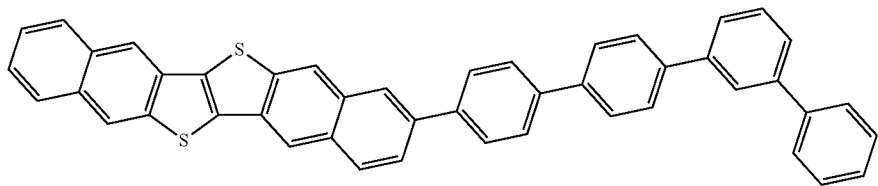
No. 17
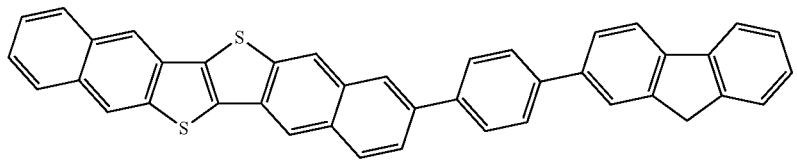
No. 18
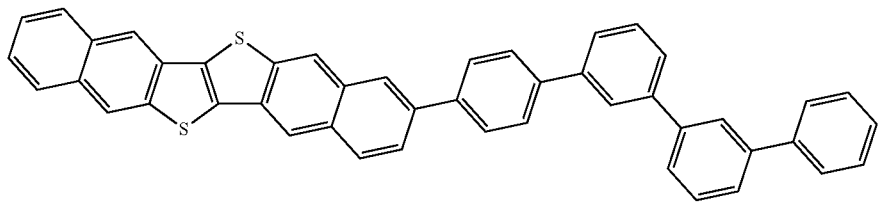
No. 19
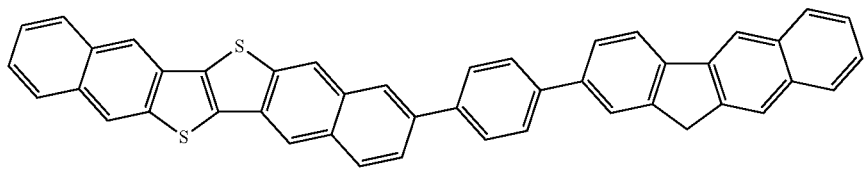
No. 20
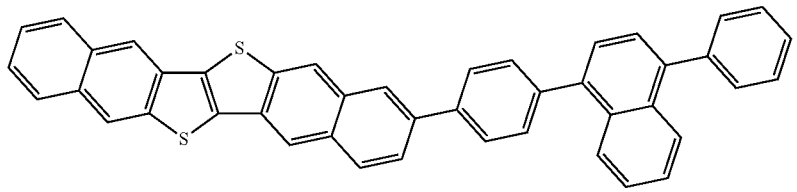
No. 21
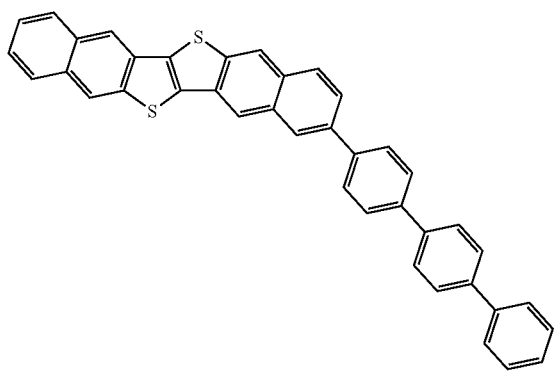
No. 22
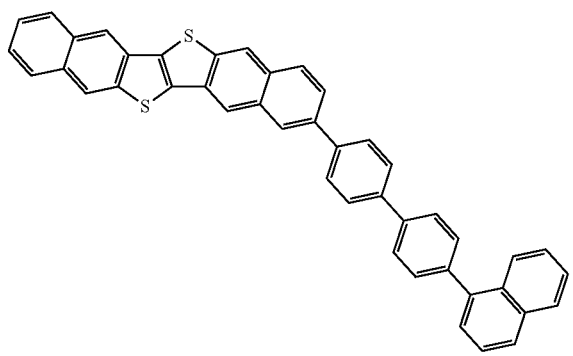

-continued
No. 23
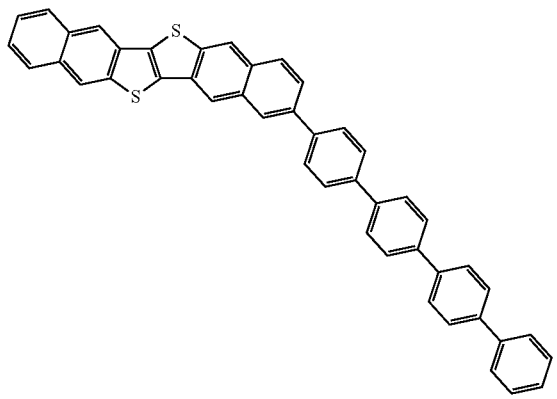
No. 24
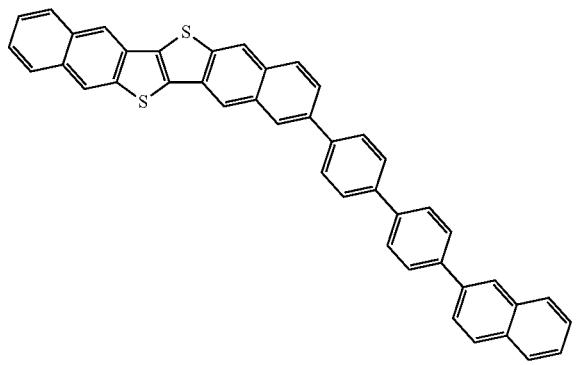
No. 25
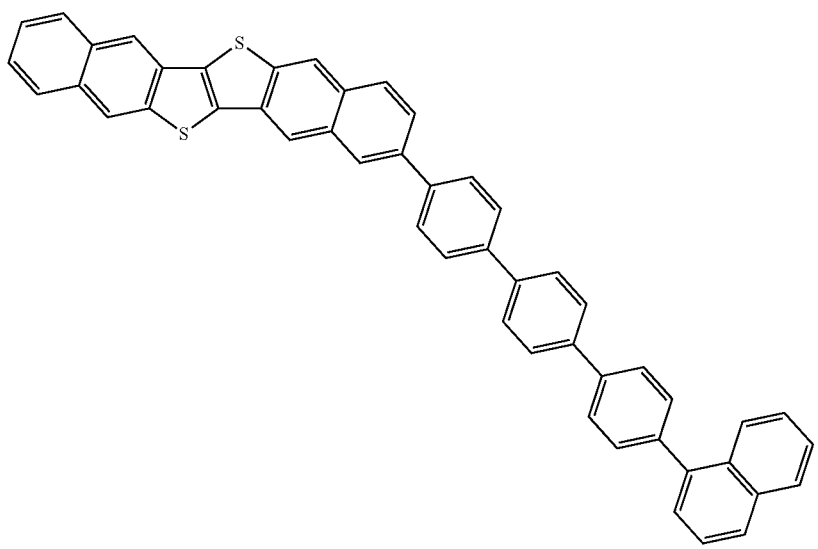
No. 26
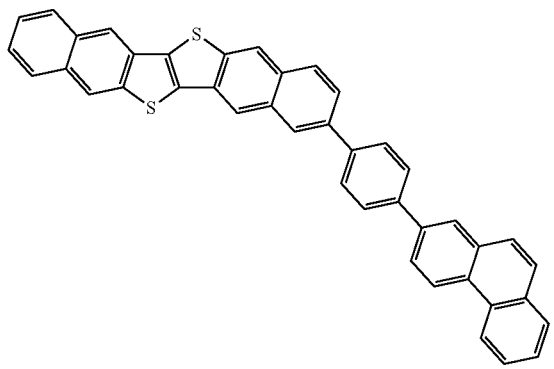
No. 27
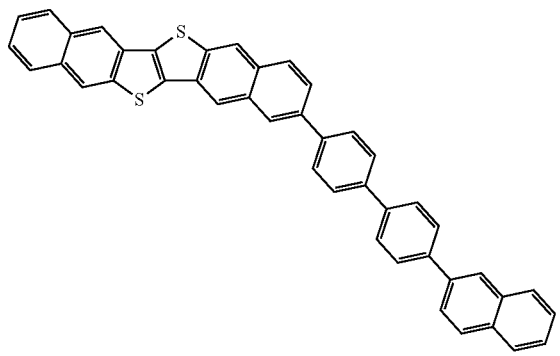

-continued
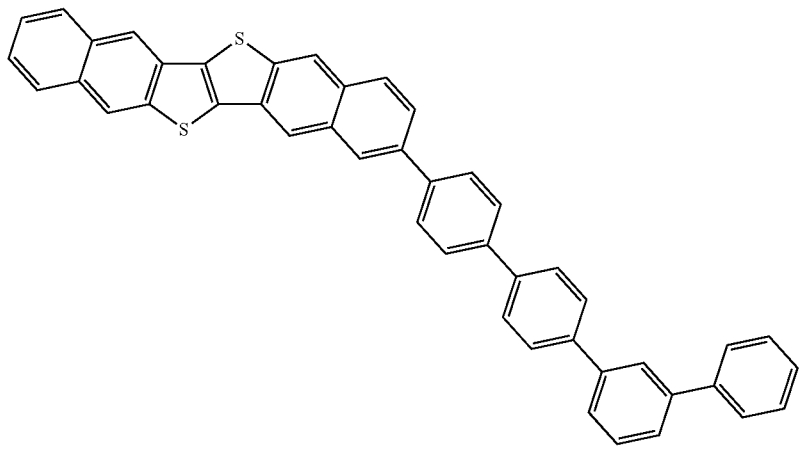
No. 28
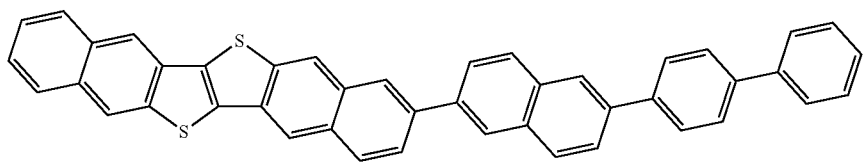
No. 29
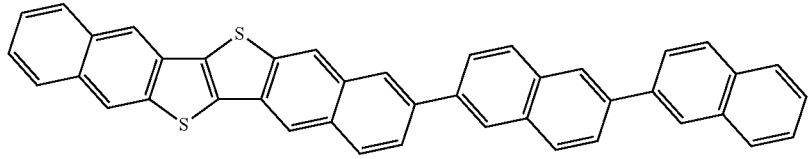
No. 30
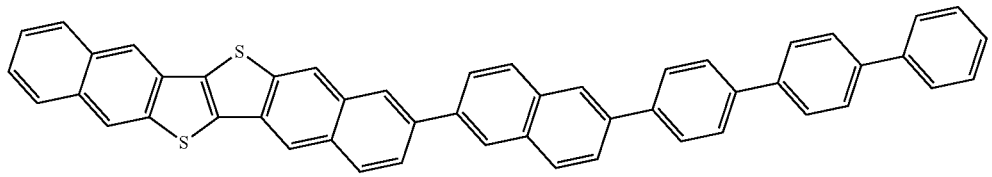
No. 31
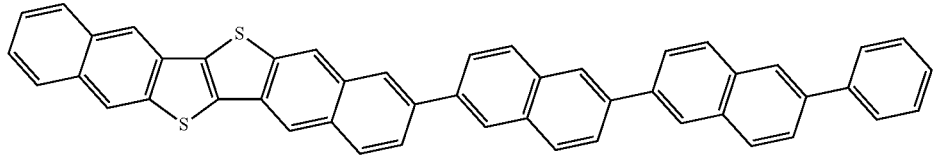
No. 32
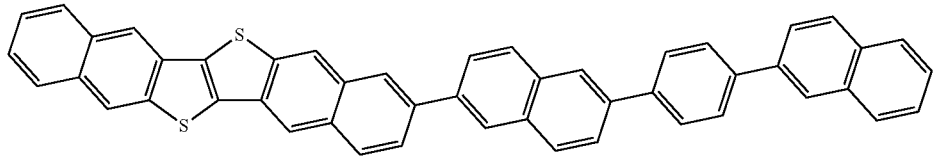
No. 33
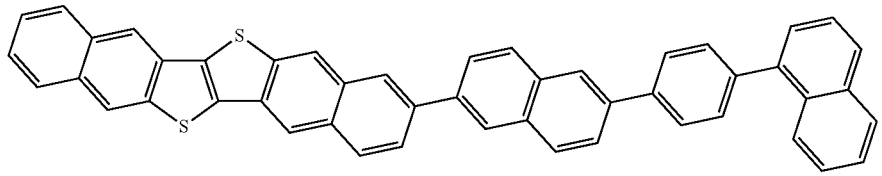
No. 34

-continued
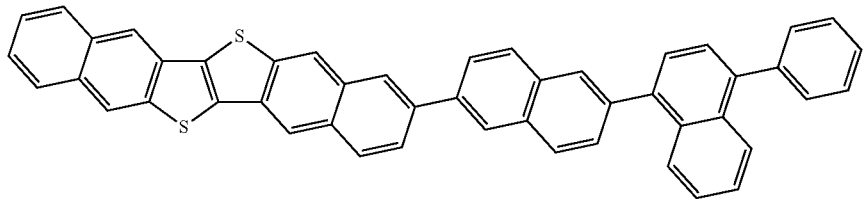
No. 35
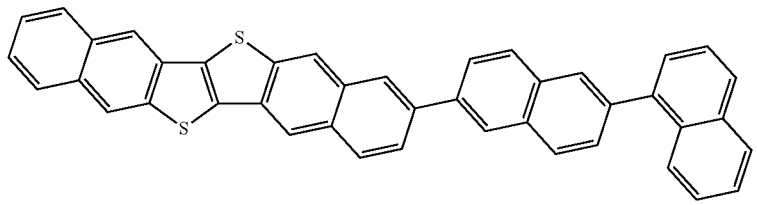
No. 36
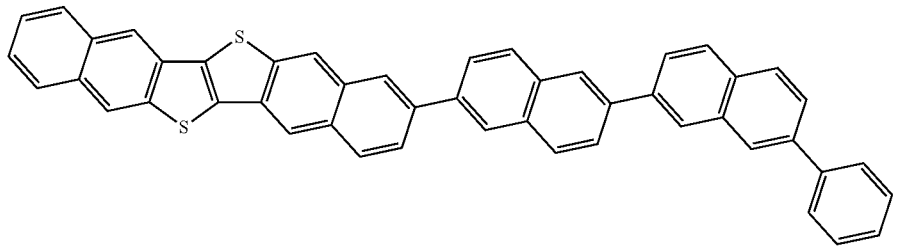
No. 37
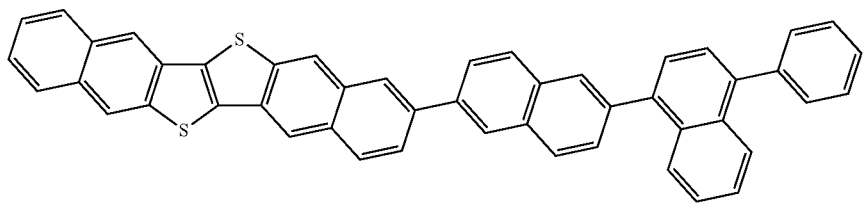
No. 38
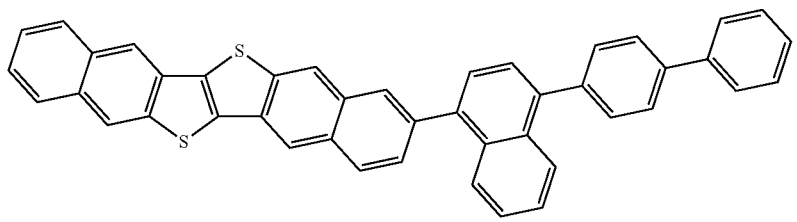
No. 39
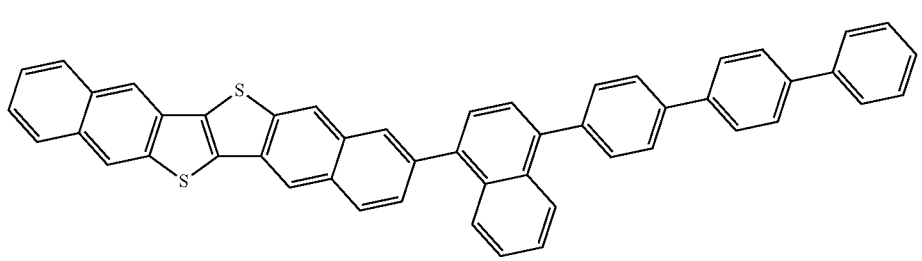
No. 40
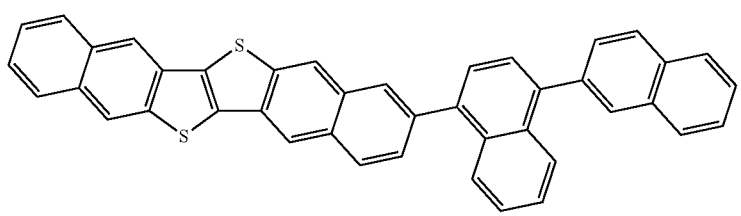
No. 41

-continued
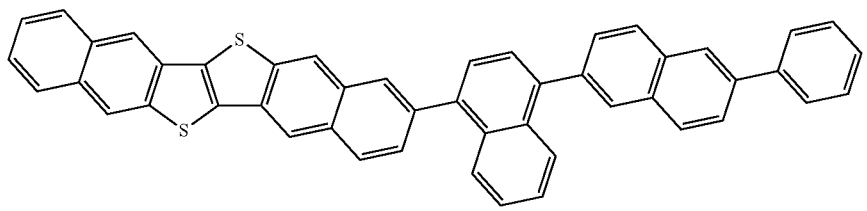
No. 42
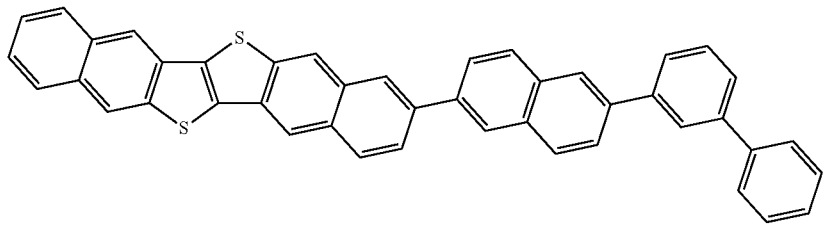
No. 43
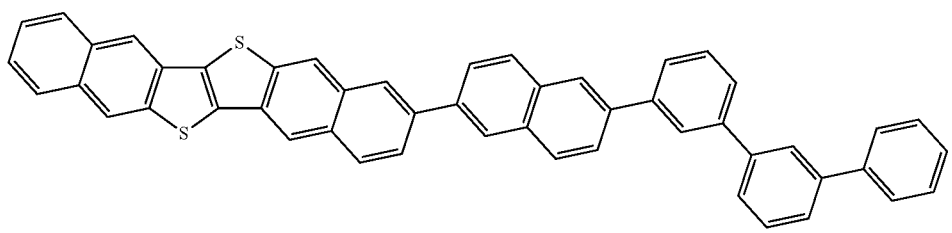
No. 44
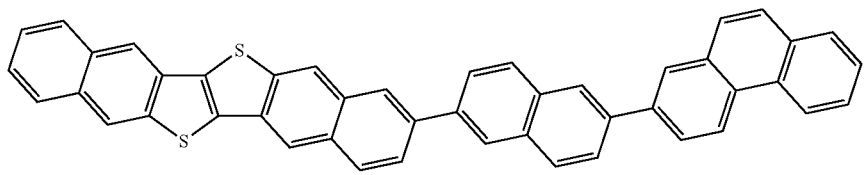
No. 45
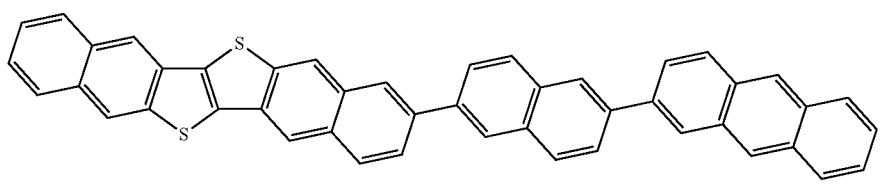
No. 46
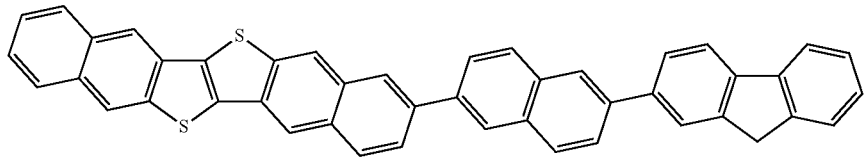
No. 47
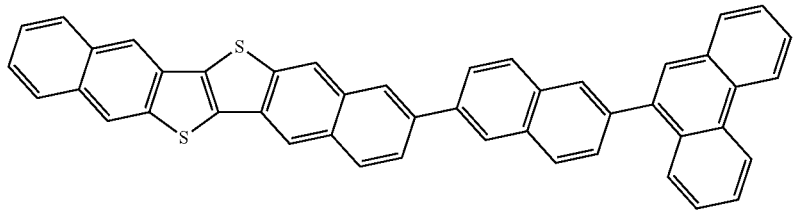
No. 48

-continued
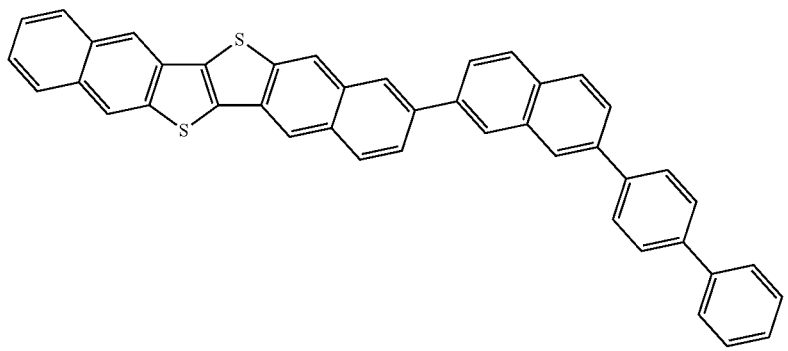
No. 49
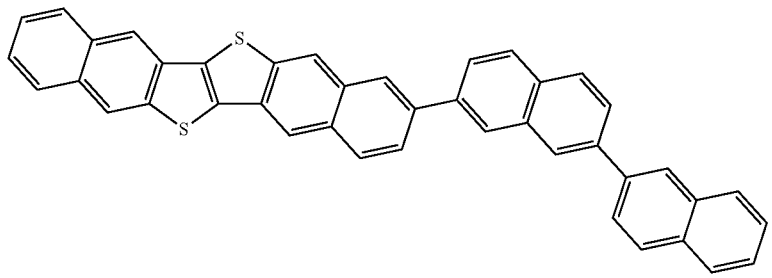
No. 50
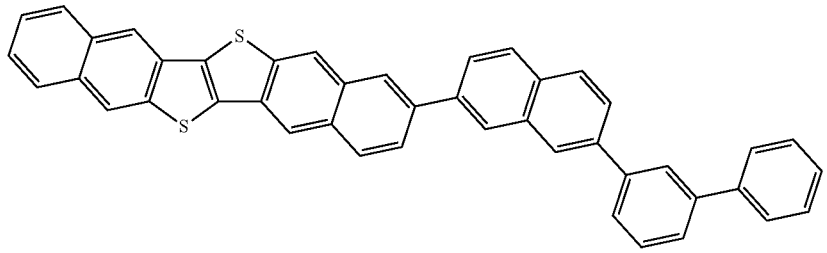
No. 51
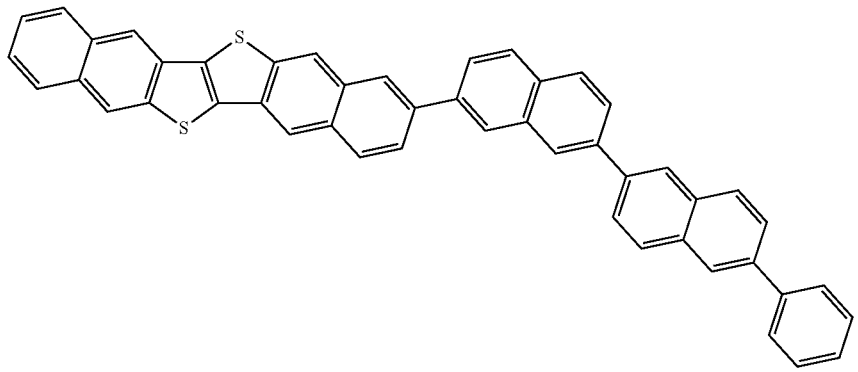
No. 52

-continued
No. 53
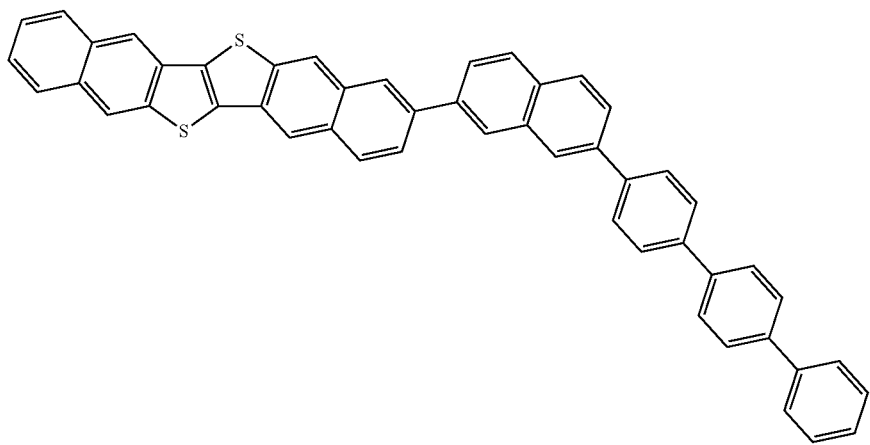
No. 54
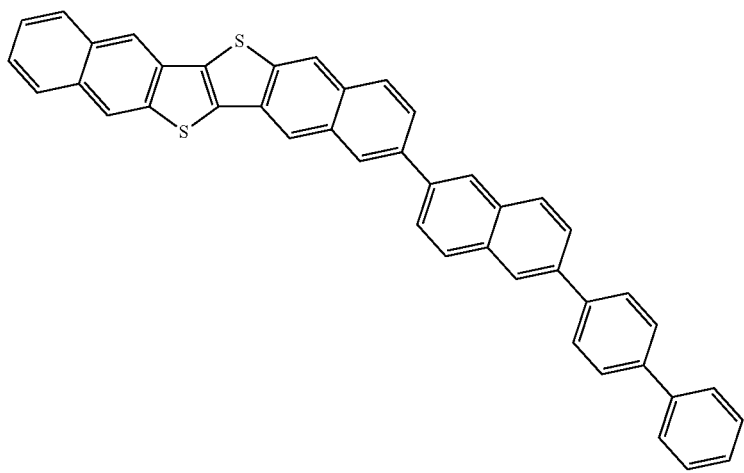
No. 55
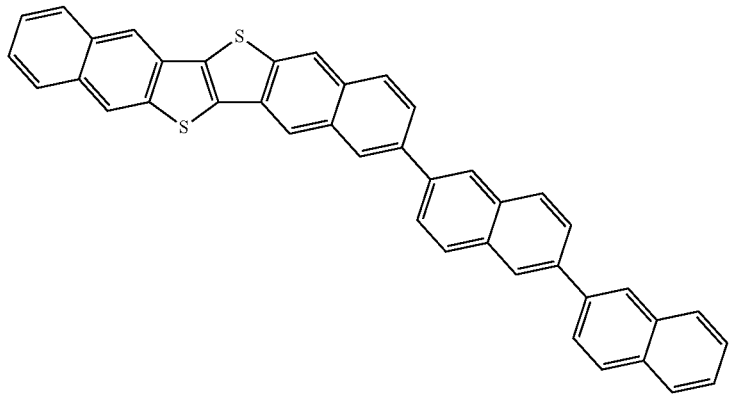

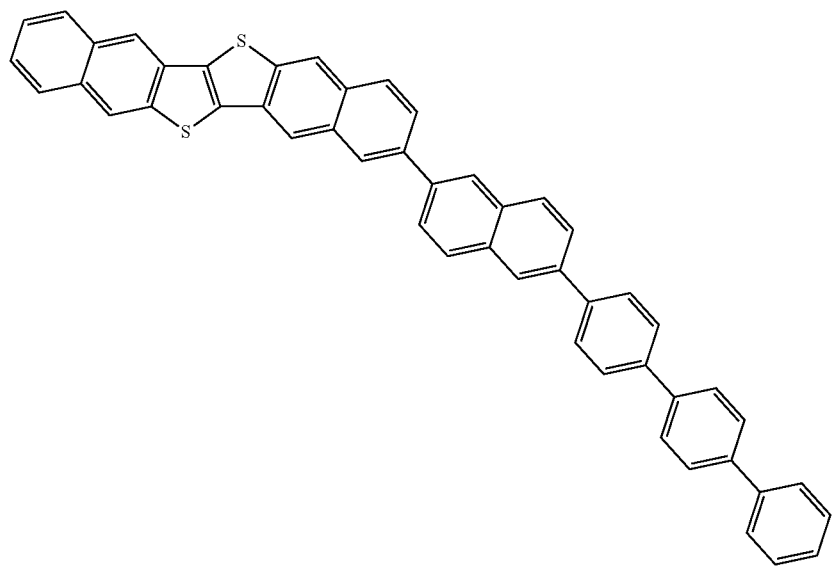
No. 56
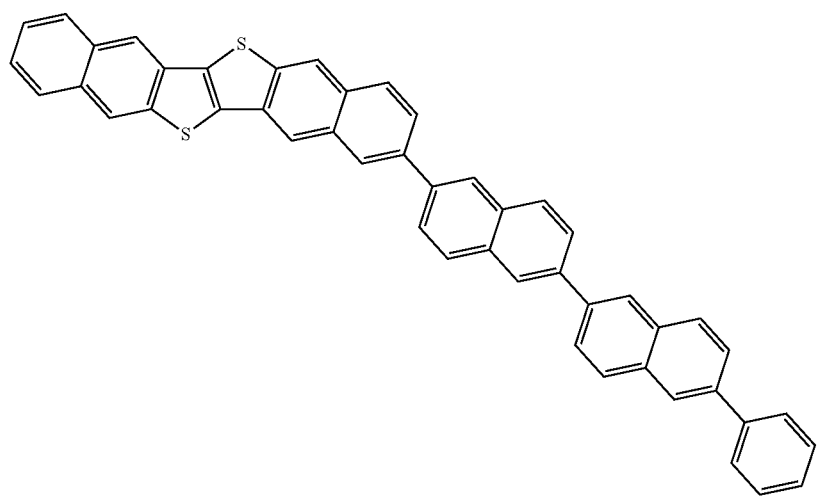
No. 57
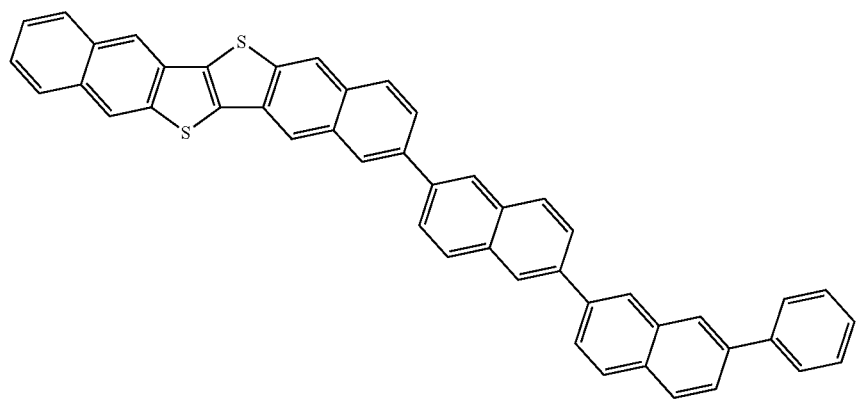
No. 58

No. 59
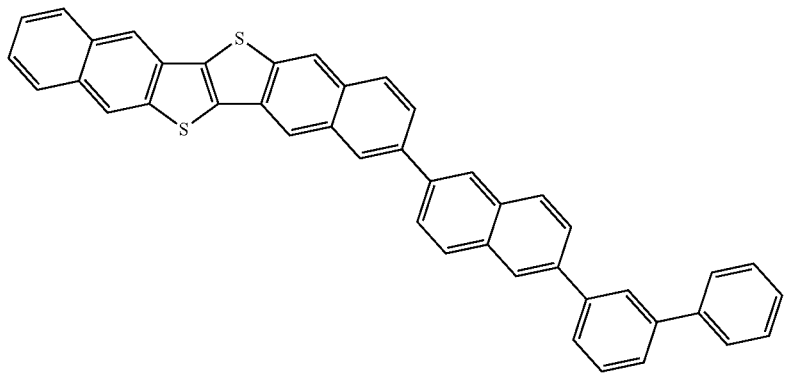
No. 60
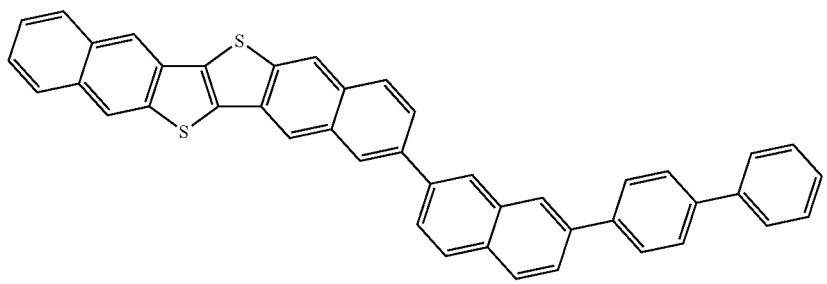
No. 61
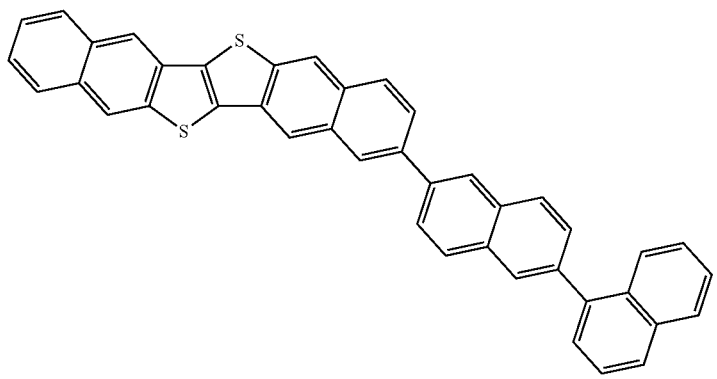
No. 62
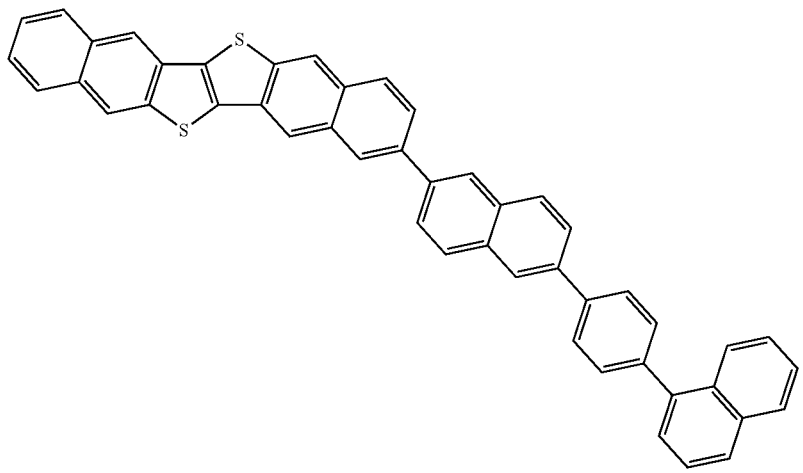

No. 63
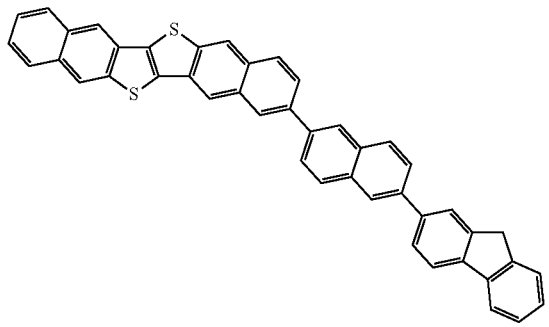

No. 64
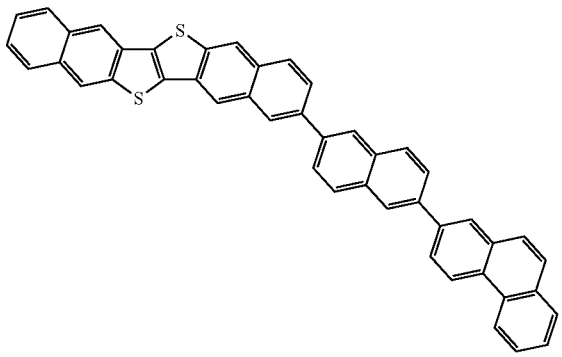

The organic thin film of the present invention contains the fused polycyclic aromatic compound represented by formula (1). The film thickness of the organic thin film differs according to the purpose, but is generally 1 nm to 1 μm, preferably 5 nm to 500 nm, more preferably 10 nm to 300 nm.

Examples of the method for forming the organic thin film include dry processes such as the vapor deposition method and various solution process, but the organic thin film is preferably formed by the solution process. Examples of the solution processes includes the spin coating method, the drop casting method, dip coating method, spray method, the letterpress printing method such as the flexographic printing, the resin letterpress printing, the lithograph printing method such as the offset printing method, the dry offset printing method, the pad printing method, the intaglio printing method such as the gravure printing method, the stencil printing method such as the screen printing method, the mimeograph printing method, the risograph printing method, the ink jet printing method, the micro contact printing method, furthermore the combination method of two or more these methods. When the film is formed by the solution process, the thin film is preferably formed by evaporating the solvent after the application or the printing aforementioned.

The field-effect transistor of the present invention controls the electric current flowing between the two electrodes (the source electrode and the drain electrode) provided in contact with the organic thin film of the present invention by applying the voltage to another electrode named the gate electrode.

For the field-effect transistor, the structure where the gate electrode is insulated by the insulator film (Metal-Insulator-Semiconductor MIS structure) is generally used. The structure using the metal oxide film as an insulator film is named MOS structure. As another structure, the structure where the gate electrode is formed through the Schottky barrier (namely the MES structure) is also known. But for the field-effect transistor, the MIS structure is often used.

Figure 1B:
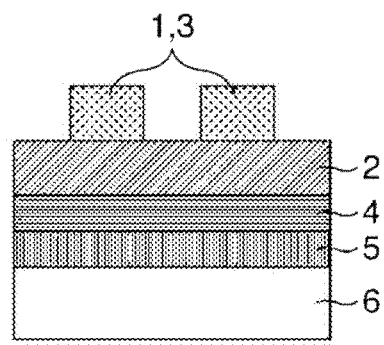
FIG. 1B is a schematic cross-sectional view of a top contact-bottom gate type field-effect transistor (element).
Figure 1C:
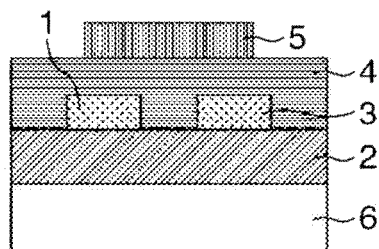
FIG. 1C is a schematic cross-sectional view of a top contact-top gate type field-effect transistor (element).
Figure 1D:
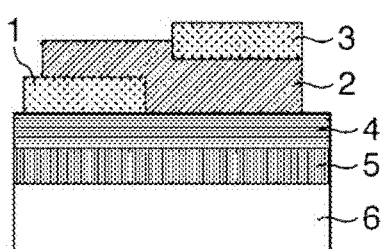
FIG. 1D is a schematic cross-sectional view of a top-and-bottom gate type field-effect transistor (element). E shows an electrostatic induction type field-effect transistor (element).
Figure 1E:
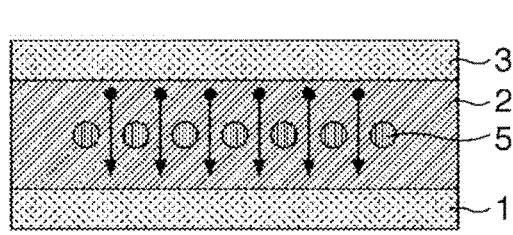
FIG. 1F is a schematic cross-sectional view of a bottom contact-top gate type field-effect transistor (element).
Figure 1F:
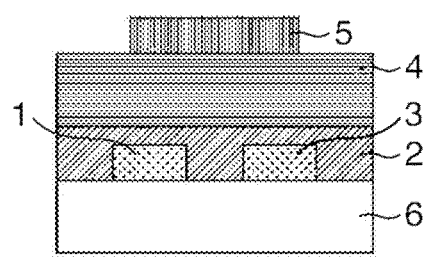

In each example of the embodiment in FIG. 1, 1 represents the source electrode, 2 represents the organic thin film (the semiconductor layer), 3 represents the drain electrode, 4 represents insulator layer, 5 represents the gate electrode, 6 represents the substrate respectively. Note that the arrangement of each layer and electrode can be appropriately selected depending on the purposes of the device. Because the electric current flow in a direction parallel to the substrate, A to D and F are called the lateral transistor. A is called the bottom contact-bottom gate structure and B is called the top contact-bottom gate structure. C is called top contact-top gate structure where the source and the drain electrodes and the insulator layer are provided on the semiconductor and the gate electrode is further formed on it. D is the structure called the top-and-bottom contact-bottom gate type transistor. F is the bottom contact-top gate structure. E is the schematic diagram of the transistor having vertical structure namely the electrostatic induction transistor (SIT). In this SIT, the flow of the electric current expands planarly, therefore a large amount of carrier can move at once. Because the source electrode and the drain electrode are arranged vertically and so the distance between the electrodes can be made small, and the response speed is high. Therefore, the SIT can be preferably adopted for the purpose such as flowing the large current and switching at high speed. Note that in FIG. 1 E, the substrate is not drawn, but the substrate is generally provided outside the source or the drain electrode represented by 1 and 3 in FIG. 1 E.

Each component of each embodiment is explained. The substrate 6 requires to hold each layer formed on it without peeling. For example, the insulating materials such as resin board, resin film, paper, glass, quartz, ceramic; the articles obtained by forming the insulating layer on the conductive substrate such as metal and alloy by the coating and the like; the materials obtained by the various combination such as the combination of the resin and the inorganic material can be used. Examples of usable resin film include polyethylene terephthalate, polyethylene naphthalate, polyethersulfone, polyamide, polyimide, polycarbonate, cellulosetriacetate and polyetherimide. When resin film and paper are used, the device has flexibility and light weight, therefore practicality improves. The thickness of the substrate is generally 1 μm to 10 mm, preferably 5 μm to 5 mm.

The material having conductivity is used for the source electrode 1, the drain electrode 3, and the gate electrode 5. For example, metals such as platinum, gold, silver, aluminum, chrome, tungsten, tantalum, nickel, cobalt, copper, iron, lead, tin, titanium, indium, palladium, molybdenum, magnesium, calcium, barium, lithium, potassium and sodium, and alloys containing these; the conductive oxides such as $InO_2$ $ZnO_2$, $SnO_2$, ITO; the conductive polymer compounds such as polyaniline, polypyrrole, polythiophene, polyacetylene, polyparaphenylenevinylene, and polydiacetylene; the semiconductors such as silicon, germanium, and gallium arsenide; the carbon materials such as carbon black, fullerene, carbon nanotube, graphite, and graphene can be used. The conductive polymer compound and semiconductor can be doped. Examples of the dopant include the inorganic acids such as hydrochloric acid, and sulfuric acid; the organic acids having acid functional group such as sulfonic acid; Lewis acids such as $PF_5$, $AsF_5$, and $FeCl_3$; halogen atoms such as iodine; metal atoms such as lithium, sodium, and potassium. Boron, phosphorus, arsenic, and the like are largely used as a dopant for the inorganic semiconductor such as silicon.

The conductive composite material obtained by dispersing carbon black, metal particle, and the like as the dopant aforementioned is also used. As for the source electrode 1 and the drain electrode 3 in contact with the semiconductor directly, selection of the appropriate work function, the surface treatment, and the like are important to reduce the contact resistance.

The distance between the source electrode and the drain electrode (channel length) is an important factor determining the characteristics of the device. The proper channel length is needed. When the channel length is short, the current amount taken out increases, but the short channel effects such as the influence of the contact resistance are generated, and the semiconductor characteristics can decline. The channel length is generally 0.01 to 300 μm, preferably 0.1 to 100 μm. The width between the source electrode and the drain electrode (channel width) is generally 10 to 5000 μm, preferably 40 to 2000 μm. The channel width can be formed further longer by forming the structure of the electrode into the comb-like structure. Depending on the current amount required and the structure of the device, the channel width needs to be made appropriate length.

Each structure (shape) of the source electrode and the drain electrode is explained. the source electrode may have the same structure as the drain electrode or the different structure from the drain electrode.

In the case of the bottom contact structure each electrode is generally manufactured by the lithography method and preferably formed in a rectangular shape. Recently the printing accuracy of various printing method has improved, the electrode can be accurately manufactured by using the methods such as the inkjet printing, the gravure printing or the screen printing. In the case of the top contact structure having the electrode on the semiconductor, the electrode can be vapor-deposited by using the shadow mask and the like. The electrode pattern can be directly formed by printing by using the method such as inkjet. The length of the electrode is the same as the channel width aforementioned above. The width of the electrode is not particularly limited but is preferably short to make the area of the device small in the range where the electrical characteristics can be stabilized. The width of the electrode is generally 0.1 to 1000 μm, preferably 0.5 to 100 μm. The thickness of the electrode is generally 0.1 to 1000 nm, preferably 1 to 500 nm, more preferably 5 to 200 nm. The electrodes 1, 3 and 5 are connected to the wiring. The wiring is manufactured from almost the same material as the electrode.

The material having insulation is used for the insulator layer 4. For example, polymers such as polyparaxylylene, polyacrylate, polymethylmethacrylate, polystyrene, polyvinylphenol, polyamide, polyimide, polycarbonate, polyester, polyvinylalcohol, polyvinylacetate, polyurethane, polysulfone, polysiloxane, polyolefin, fluoro resin, epoxy resin and phenol resin and the copolymer consisting of a combination thereof; metal oxides such as silicon oxide, aluminum oxide, titanium oxide, and tantalum oxide; the ferroelectric metal oxides such as $SrTiO_3$, and $BaTiO_3$; the dielectric such as nitrides such as silicon nitride and aluminum nitride, sulfide and fluoride: or the polymer dispersed with these dielectric particles and the like can be used. The insulator layer having high electrical insulating characteristics can be preferably used to reduce the leak current. By using the insulator layer having high electrical insulating characteristics the thickness of the film can be reduced. The insulating capacitance can increase, and the current taken out can increase. To improve the mobility of the semiconductor, the surface energy on the surface of the insulator layer is preferably reduced. The smooth film having no unevenness is preferable. For that purpose, the self-assembled monomolecular film or the insulator layer having two layers is sometimes formed. The thickness of the insulator layer 4 is different depending on the material, but generally 0.1 nm to 100 μm, preferably 0.5 nm to 50 μm, more preferably 1 nm to 10 μm.

The fused polycyclic aromatic compound of the present invention is used for the material for the semiconductor layer 2. The organic semiconductor film can be formed by the method equivalent to the method shown above for forming the organic semiconductor film and used as the semiconductor layer 2.

As for the semiconductor layer (the organic thin film), a plurality of the layer may be formed but single-layer structure is more preferable. The thinner film thickness of the semiconductor layer is in the range where the necessary function is not lost, the more preferable the film thickness is. As for the horizontal field-effect transistor shown by A, B and D, the device characteristics do not depend on the film thickness of the film as long as the semiconductor layer has the film thickness more than the thickness prescribed. It is because the leakage current often increases when the thickness of the film become thick. The thickness of the semiconductor layer to exhibit the necessary function is generally 1 nm to 1 μm, preferably 5 nm to 500 nm, more preferably 10 nm to 300 nm.

For the field-effect transistor, another layer can be provided, for example, between the substrate layer and the insulator film layer, between the insulator film layer and the semiconductor layer, or outside the device when necessary. For example, when the protective layer is provided on the organic thin film directly or on another layer provided on the organic thin film, the effects of the outside air such as humidity can be reduced. There are the advantages to stabilize the electrical characteristics such as the advantage that the on/off ratio of the field-effect transistor can increase.

The material for the protective layer aforementioned is not limited. But for example, the films formed of various resins such as epoxy resin, acryl resins such as polymethylmethacrylate, polyurethane, polyimide, polyvinylalcohol, fluoro resin, polyolefin; the films formed of the inorganic oxide such as silicon oxide, aluminum oxide, and silicon nitride; the films formed of the dielectric such as the nitride film are preferably used. The resin (polymer) having low transmittance of oxygen and water and low water absorption is especially preferable. The gas barrier protective material developed for the organic EL display also can be used. The film thickness of the protective layer can be selected according to the purpose, but generally 100 nm to 1 mm.

The characteristics as the field-effect transistor can be improved by performing the surface modification or the surface treatment in advance on the substrate or the insulator layer laminated with the organic thin film. For example, by adjusting the ratio of the hydrophilicity to hydrophobicity of the substrate surface, the film quality and the film formation of the film formed on the substrate can be improved. Especially the characteristics of the organic semiconductor material may vary greatly depending on the film condition such as the molecular orientation. Therefore, by the surface treatment of the substrate, the insulator layer and the like the molecular orientation of the interface part with the organic thin film formed after the treatment is controlled, or the trap site on the substrate or the insulator layer decreases, so the characteristics such as the carrier mobility may be improved.

The trap site refers to the functional groups such as hydroxy group existing on the untreated substrate. When these functional groups exist, the electron is drawn to said functional group, as a result the carrier mobility decreases. Therefore, decreasing the trap site is often effective for improving the characteristics such as the carrier mobility, too.

Examples of the surface treatment aforementioned to improve the characteristics include the self-assembled monomolecular film treatment by using hexamethyldisilazane, octyltrichlorosilane, octadecyltrichlorosilane and the like; the surface treatment by using polymer and like; the acid treatment by using hydrochloric acid, sulfuric acid, acetic acid and the like; the alkali treatment by using sodium hydroxide, potassium hydroxide, calcium hydroxide, ammonia, and the like; the ozone treatment; the fluorination treatment; the plasma treatment by using oxygen, argon, and the like; the Langmuir-Blodgett film forming treatment; the treatment forming the thin film such as another insulator and semiconductor; the mechanical treatment; the electrical treatment such as the corona discharge; the rubbing treatment by using the fiber and the like. The combination of these treatments also can be performed.

In these embodiments as the method for forming each film such as the film between the substrate layer and the insulator film layer and the film between the insulator film layer and the organic thin film, the vacuum process and the solution process aforementioned can be adopted according to circumstances.

Next, the method for manufacturing the field-effect transistor of the present invention is described below based on FIG. 2 by using the top contact-bottom gate type field-effect transistor shown in FIG. 1 embodiment example B as an example. This manufacturing method can be also adopted for the field-effect transistors of other embodiments aforementioned and the like.

(Substrate and Substrate Treatment of Field-Effect Transistor)

The field-effect transistor of the present invention is manufactured by providing necessary various layers and electrodes on the substrate 6 (see FIG. 2 (1)). The substrate explained above can be used. The surface treatment and the like above also can be performed on the substrate. The thickness of the substrate 6 is preferably thin within the range not disturbing the necessary function. The thickness is different depending on the material, but is generally 1 µm to 10 mm, preferably 5 µm to 5 mm. The substrate also can have the functions of the electrode, when necessary.

(Formation of Gate Electrode)

The gate electrode 5 is formed on the substrate 6 (see FIG. 2 (2)). The electrode material explained above can be used. Various method can be used as the method for forming the electrode film. For example, the vacuum vapor deposition method, the sputtering method, the application method, the heat transfer method, the printing method, the sol-gel method and the like are adopted. During or after forming the film, the patterning is preferably performed to form the film having the form required if necessary. Various methods also can be used as the method for patterning. The patterning method include photolithography method combining the patterning and the etching of the photoresist. The patterning also can be performed by using the vapor deposition method using the shadow mask, the sputtering method, the printing method such as the inkjet printing, the screen printing, the offset printing, and the letterpress printing, the soft lithography method such as the micro contact printing method, and the method combining two or more these methods. The thickness of the gate electrode 5 is different depending on the material, but is generally 0.1 nm to 10 µm, preferably 0.5 nm to 5 µm, more preferably 1 nm to 3 µm. When the gate electrode double as the substrate, the thickness can be thicker than the thickness aforementioned.

(Formation of Insulator Layer)

The insulator layer 4 is formed on the gate electrode 5 (see FIG. 2 (3)). The insulator material aforementioned is used. Various methods can be used for forming the insulator layer 4. Examples of the methods include the application methods such as the spin coating, the spray coating, the dip coating, the cast, the bar coating, the blade coating, the printing methods such as the screen printing, the offset printing, the ink jet printing, the dry process method such as the vacuum vapor deposition method, the molecular beam epitaxial growth method, the ionized cluster beam method, the ion plating method, the sputtering method, the atmospheric pressure plasma method, the CVD method. In addition, the sol-gel method, the method forming the oxide film on the metal by the thermal oxidation method such as the aluminum oxide film on aluminum, and the silicon oxide film on silicon, and the like are adopted. Note that on the interface where the insulator layer is in contact with the semiconductor layer, the surface treatment prescribed for the insulator layer also can be performed to orient the molecule of the compound composing the semiconductor on the interface of both layers well. The same surface treatment method as the surface treatment for the substrate can be used. Because increasing the electric capacity increases the amount of the electricity taken out, the film thickness of the insulator layer is preferably as thin as possible. In case of thin film, the leak current increases, so the film thickness is preferably thin within the range not disturbing the function. The film thickness is generally 0.1 nm to 100 µm, preferably 0.5 nm to 50 µm, more preferably 5 nm to 10 µm.

(Formation of Organic Thin Film)

Various methods such as the application method and the printing method can be used for forming the organic thin film (the organic semiconductor layer). Examples include the forming method by solution process such as the application methods such as the dip coating method, the die coating method, the roll coating method, the bar coating method, and the spin coating method, the inkjet method, the screen printing method, the offset printing method, and the micro contact printing method.

The method for obtaining the organic thin film by forming the film by the solution process is explained. The organic semiconductor composition is applied on the substrate (the exposed parts of the insulator layer, the source electrode, and the drain electrode). Examples of the application method include the spin coating method, the drop casting method, the dip coating method, the spray coating method, the letterpress printing methods such as the flexographic printing, the resin letterpress printing, the lithographic printing methods such as offset printing method, the dry offset printing method, the pad printing method, the intaglio printing methods such as the gravure printing method, the stencil printing methods such as the silk screen printing method, the mimeograph printing method, and the risograph printing method, the inkjet printing method, the micro contact printing method, and the method combining two or more these methods.

As the method similar to the application method, the Langmuir-Blodgett method where the monomolecular film of the organic thin film manufactured by dropping the composition aforementioned on the surface of the water is transferred on the substrate to laminate and the method where the liquid crystal or the molten material is introduced between two substrates by using the capillary phenomenon can be adopted.

The environment such as the temperature of the substrate and the composition during forming the film is also important. Because the characteristics of the field-effect transistor may vary according to the temperatures of the substrate and the composition, the temperatures of the substrate and the composition are preferably carefully selected. The temperature of the substrate is generally 0 to 200° C., preferably 10 to 120° C., more preferably 15 to 100° C. Because the temperature greatly depends on the solvent and the like in the composition used, the caution should be required.

The film thickness of the organic thin film manufactured by the method is preferably thin within the range not disturbing the function. Increasing the film thickness may increase the leak current, which provides concern. Therefore, the film thickness of the organic thin film is generally 1 nm to 1 μm, preferably 5 nm to 500 nm, more preferably 10 nm to 300 nm.

The characteristics of the organic thin film (see FIG. 2 (4)) formed in this manner can further be improved by the aftertreatment. For example, by performing the heat treatment as the aftertreatment, the distortion generated in the film during formation of the film can be reduced, the pinhole can be reduced, the arrangement and the orientation in the film can be controlled, so the improvement and stabilization of the characteristics of the organic semiconductor can be achieved. Performing the heat treatment is effective for improving the characteristics when manufacturing the field-effect transistor of the present invention. The heat treatment is performed by heating the substrate after forming the organic thin film. The temperature of the heat treatment is not limited, but generally from room temperature to about 180° C., preferably 40 to 160° C., further preferably 45 to 150° C. The heat treatment time is not limited, but generally 10 seconds to 24 hours, preferably 30 seconds to about 3 hours. The heat treatment may be performed in the air or under the inert atmosphere such as nitrogen and argon. Besides, the control of the film form by the solvent vapor and the like can be taken.

By treating with the oxidizing or the reducing gas such as oxygen and hydrogen, the oxidizing or the reducing liquid or the like as another aftertreatment, the change of the characteristics by the oxidization or the reduction can be induced. The treatment can be used to increase or decrease the carrier density in the film, for example.

In the method referred to as the doping an element, an atom group, a molecule or a polymer can be added to the organic thin film in a small amount to change the characteristics of the organic thin film. For example, the acids such as oxygen, hydrogen, hydrochloric acid, sulfuric acid, and sulfonic acid; the Lewis acids such as $PF_5$, $AsF_5$, and $FeCl_3$; the halogen atoms such as iodine; the metal atoms such as sodium and potassium; the doner compounds such as tetrathiafulvalene (TTF) and phthalocyanine can be added for doping. The doping can be achieved by bringing these gases into contact with the organic thin film, dipping the organic thin film into the solution, and performing the electrochemical doping treatment for the organic thin film. The doping can be performed not only after manufacturing the organic thin film but also by addition of the donor compound during synthesizing the organic semiconductor compound, addition of the donor compound to the organic semiconductor composition, and addition at the step forming the organic thin film and the like. Furthermore, the doping can be performed by vapor depositing together by adding the material used for the doping to the material for forming the organic thin film during vapor depositing, mixing the doping material into the surrounding atmosphere gas when manufacturing the organic thin film (manufacturing the organic thin film under the environment where the doping material exist), and accelerating the ion in a vacuum to collide with the film.

The effects of the doping include the change of the electroconductivity by the increase or the decrease of the carrier density, the change of the polarity of the carrier (p type, n type) and the change of the Fermi level.

(Formation of Source Electrode and Drain Electrode)

The source electrode 1 and the drain electrode 3 can be formed according to the method equivalent to the method in the case of the gate electrode 5 (see FIG. 2 (5)). Various additives can be used to reduce the contact resistance with the organic thin film.

(Protective Layer)

Forming the protective layer 7 on the organic thin film has the advantage that the influence of the outside air can be minimized and the electric characteristics of the field-effect transistor can be stabilized (see FIG. 2 (6)). The material aforementioned is used for the protective layer. The film thickness of the protective layer 7 is adopted at random according to the purpose, but generally 100 nm to 1 mm.

Various methods can be adopted for forming the film for the protective layer. When the protective layer consists of the resin, the method for forming the protective layer includes the method where the resin film is formed by drying after applying the resin solution; and the method where the resin monomer is polymerized after applying or vapor depositing. After forming the film, cross-linking treatment may be performed. When the protective layer consists of the inorganic substance, the forming method by the vacuum processes such as the sputtering method and the vapor deposition method and the forming method by the solution processes such as the sol-gel method also can be used.

For the field-effect transistor, if necessary, the protective layer can be provided between each layer as well as on the organic thin film. These layers may be useful to stabilize the electric characteristics of the field-effect transistor.

The field-effect transistor also can be used as digital devices such as the memory circuit device, the signal driver circuit device, and the signal processing circuit device and the analog device. By combining these devices, the display, the IC card, the IC tag and the like can be manufactured. Furthermore, because the characteristics of the field-effect transistor can be changed by the external stimuli such as the chemical substance, the field-effect transistor can be used as the sensor, too.

The material for the organic photoelectric conversion element of the present invention contains the fused polycyclic aromatic compound represented by above formula (1). The content of the fused polycyclic aromatic compound represented by formula (1) in the material for the organic photoelectric conversion element of the present invention is not particularly limited as long as the performance required for the purpose for which the material for the organic photoelectric conversion element is used exhibits, but generally equal to or more than 50% by mass, preferably equal to or more than 80% by mass, more preferably equal to or more than 90% by mass, further preferably equal to or more than 95% by mass. The other compound except for the compound represented by formula (1) (for example, the material for the organic photoelectric conversion element except for the compound represented by formula (1) and the like), the additive, and the like can be used together with the material for the organic photoelectric conversion element of the present invention. The compound, the additive and the like capable of using together is not particularly limited as long as the performance required for the purpose for which the material for the organic photoelectric conversion element is used exhibits.

The organic photoelectric conversion element of the present invention has the organic thin film of the present invention. The organic photoelectric conversion element is the element wherein the photoelectric conversion part (film) is provided between a pair of the opposed electrode films and the light enters the photoelectric conversion part from the area over the electrode film. Because the photoelectric conversion part generates electrons and positive holes according to the entering of the light and the signal can be read out according to the charge of the electrons or the positive holes by the semiconductor, the organic photoelectric conversion element can show the amount of the incident light according to the absorption wavelength of the photoelectric conversion film part. The transistor for reading out may be connected to the electrode film which the light does not enter. When a number of the organic photoelectric conversion element are provided in an array, the incident position information is shown as well as the amount of the incident light. Therefore, the organic photoelectric conversion element becomes the imaging element. When the organic photoelectric conversion element provided closer to the light source dose not shield the absorption wavelength (let the absorption wavelength pass through) of the organic photoelectric conversion element provided behind it from the light source, a plurality of the organic photoelectric conversion element can be laminated to use.

For the organic photoelectric conversion element of the present invention, the organic thin film containing the fused polycyclic aromatic compound represented by above formula (1) is used as the constituent material of the photoelectric conversion part.

The photoelectric conversion part often consists of the photoelectric conversion layer and one or more of the organic thin film layers except for the photoelectric conversion layer selected from a group consisting of the electron transport layer, the positive hole transport layer, the electron block layer, the positive hole block layer, the crystallization preventive layer, the interlayer contact improving layer, and the like. The fused polycyclic aromatic compound of the present invention preferably is used as the organic thin film layer of the photoelectric conversion layer, but also can be used as the organic thin film layer aforementioned (especially the electron transport layer, the positive hole transport layer, the electron block layer, the positive hole block layer). The electron block layer and the positive hole block are also referred to the carrier block layer. When the fused polycyclic aromatic compound is used for the photoelectric conversion layer, the photoelectric conversion layer may consist of only the fused polycyclic aromatic compound of the present invention, but may contain the organic semiconductor material also the fused polycyclic aromatic compound of the present invention. These organic thin film layer may have lamination structure, but may contain the organic thin film formed by co-vapor deposing the material and in addition, may be the organic thin film formed by forming plural layers with the co-vapor deposition film, the mono-film or the other co-vapor deposition film to function.

The electrode film used for the organic photoelectric conversion element of the present invention plays the role of taking out and collecting the positive holes from said photoelectric conversion layer or the other organic thin film layer, when the photoelectric conversion layer in the photoelectric conversion part described below have positive hole transporting property and when the organic thin film except for the photoelectric conversion layer is the positive hole transport layer having positive hole transporting property. The electrode film used for the organic photoelectric conversion element play the role of taking out and emitting the electron from said photoelectric conversion layer or the other organic thin film layer, when the photoelectric conversion layer in the photoelectric conversion part have electron transporting property and when the organic thin film except for the photoelectric conversion layer is the electron transport layer having electron transporting property. Therefore, the material capable of using for the electrode film is not particularly limited as long as the material has a certain degree of conductivity, but is preferably selected in consideration of adhesion and electron affinity with the adjacent photoelectric conversion layer and the other organic thin film, ionization potential, stability, and the like. The material capable of using for the electrode film include conductive metal oxide such as tin oxide (NESA), indium oxide, indium tin oxide (ITO), and indium zinc oxide (IZO); metal such as gold, silver, platinum, chrome, aluminum, iron, cobalt, nickel, and tungsten; inorganic conductive substance such as copper iodide and copper sulfide; conductive polymer such as polythiophene, polypyrrole, and polyaniline; carbon. These materials may be used in mixture of two or more and two or more materials may be used by laminating to become two or more layers if necessary. The conductivity of the material used for the electrode film is not also particularly limited as long as the organic photoelectric conversion element is not prevented from receiving light more than necessary, but is preferably as high as possible from the point of view of the signal strength of the organic photoelectric conversion element and the electricity consumption. For example the conductive ITO film having the sheet resistance equal to or less than 300Ω/□ sufficiently functions as an electrode film. But the substrate having the conductive ITO film having the sheet resistance of about several Ω/□ are commercially available, so the substrate having such high conductivity is preferably used. The thickness of ITO film (the electrode film) can be selected randomly in consideration of conductivity, but generally about 5 to 500 nm, preferably about 10 to 300 nm. Examples of the method for forming the film such as ITO include conventional well-known vapor deposition methods, the electron beam method, the sputtering method, the chemical reaction method, and the application method. The UV-ozone treatment, the plasma treatment and the like may be performed to the ITO film provided on the substrate if necessary.

Among the electrode films, examples of the material for the transparent electrode film used for at least either of the light incident side include ITO, IZO, $SnO_2$, ATO (antimony-doped tin oxide), ZnO, AZO (aluminum-doped zinc oxide), GZO (gallium-doped zinc oxide), $TiO_2$, and FTO (fluorine-doped tin oxide). The transmittance of the incident light through the transparent electrode film at the absorption peak wavelength of the photoelectric conversion layer is preferably equal to or more than 60%, more preferably equal to or more than 80%, and most preferably equal to or more than 95%.

When a plurality of the photoelectric conversion layer having different detection wavelengths are laminated, the electrode film (the electrode film except for a pair of the electrode films aforementioned) used between each photoelectric conversion layer needs to transmit the light having a wavelength except for the wavelength of the light detected by each photoelectric conversion layer. The material transmitting equal to or more than 90% of the incident light is preferably used for said electrode film, the material transmitting equal to or more than 95% of the incident light is more preferably used for said electrode film.

The electrode film is preferably manufactured under plasma-free conditions. Manufacturing these electrode films under plasma-free conditions decreases the effect of the plasma on the substrate on which the electrode film is provided and improves the photoelectric conversion property of the photoelectric conversion element. Here the plasma-free conditions are meant to be no plasma or decreased plasma getting to the substrate because of the distance between the plasma generation source and the substrate of equal to or more than 2 cm, preferably 10 cm, further preferably 20 cm.

Examples of the apparatus not generating the plasma during formation of the electrode film include the electron beam vapor deposition apparatus (EB vapor deposition apparatus) and the pulse laser vapor deposition apparatus. The method for forming the transparent electrode film by using the EB vapor deposition apparatus is referred to the EB vapor deposition method, and the method for forming the transparent electrode film by using the pulse laser vapor deposition apparatus is referred to the pulse laser vapor deposition method.

Examples of the apparatus realizing the condition where the plasma is decreased during forming the film (hereinafter referred to the plasma-free film forming apparatus) include the facing target type sputtering apparatus and the arc plasma vapor deposition apparatus.

When the transparent conductive film is used as the electrode film (for example, the first conductive film), the DC short or the increase of the leak current may occur. One of the reasons is thought to be that the minute crack generated in the photoelectric conversion layer is covered by the elaborate film such as TCO (Transparent Conductive Oxide) and the conduction with the electrode film on the opposite side of the transparent conductive film increases. Therefore, when the material having the relatively poor film quality such as Al is used for the electrode film, the leak current dose not increase. The increase of the leak current can be suppressed by controlling the film thickness of the electrode film according to the film thickness of the photoelectric conversion layer (the depth of the crack).

Generally, when the conductive film becomes thinner than the prescribed value of the thickness, the resistance value increases sharply. The sheet resistance of the conductive film in the photoelectric conversion element for the photosensor of the present embodiment is generally 100 to 10,000Ω/□ and the degree of the freedom of the film thickness is large. The thinner the transparent conductive film is, the less the amount of the light absorbed is. Generally, the light transmittance becomes high. When the transmittance becomes high, the amount of the light absorbed by the photoelectric conversion layer increases and the photoelectric conversion performance is improved, which is very preferable.

The photoelectric conversion part contained in the organic photoelectric conversion element of the present invention may contain the photoelectric conversion layer and the organic thin film layer except for the photoelectric conversion layer. For the photoelectric conversion layer of the photoelectric conversion part, the organic semiconductive film is generally used. The organic semiconductor layer may be one or more layers. When the organic semiconductor layer is one layer, the P type organic semiconductor layer, the N type organic semiconductor layer or the mixture thereof (the bulk hetero structure) is used. When the organic semiconductor layer is a plural number of layers, the number of the layer is about 2 to 10. The organic semiconductor layer has the structure obtained by laminating one or more of the P type organic semiconductor layer, the N type organic semiconductor layer and the mixture film thereof (the bulk hetero structure). The buffer layer may be inserted between the layers. The thickness of the photoelectric conversion layer is generally 50 to 500 nm.

For the organic semiconductor film of the photoelectric conversion layer according to the wavelength range absorbed, triarylamine compound, benzidine compound, pyrazoline compound, styrylamine compound, hydrazone compound, triphenylmethane compound, carbazole compound, polysilane compound, thiophene compound, phtharocyanine compound, cyanine compound, merocyanine compound, oxonol compound, polyamine compound, indole compound, pyrrole compound, pyrazole compound, polyarylene compound, carbazole derivative, naphthalene derivative, anthracene derivative, chrysene derivative, phenanthrene derivative, pentacene derivative, phenylbutadiene derivative, styryl derivative, quinoline derivative, tetracene derivative, pyrene derivative, perylene derivative, fluoranthene derivative, quinacridone derivative, coumalin derivative, polyphyrine derivative, fullerene derivative, metal complex (Ir complex, Pt complex, Eu complex and the like) and the like can be used. According to the combination with the fused polycyclic aromatic compound of the present invention, the organic semiconductor film function as the P type organic semiconductor or the N type organic semiconductor.

When the fused polycyclic aromatic compound of the present invention is used for the photoelectric conversion layer, the fused polycyclic aromatic compound of the present invention preferably has shallower HOMO (Highest Occupied Molecular Orbital) level than the HOMO level of the organic semiconductor combined with aforementioned. As a result, not only the generation of the dark current can be suppressed but also the photoelectric conversion efficiency can be improved.

In the organic photoelectric conversion element of the present invention, the organic thin film layer of the photoelectric conversion part except for the photoelectric conversion layer is also used as the layer except for the photoelectric conversion layer for example, the electron transport layer, the positive hole transport layer, the electron block layer, the positive hole block layer, the crystallization preventive layer, the interlayer contact improving layer and the like. Especially by using as the one or more thin film layer selected from the group consisting of the electron transport layer, the positive hole transport layer, the electron block layer, and the positive hole block layer, the element capable of efficiently converting even weak light energy into the electric signal can be obtain, which is preferable.

The electron transport layer has the roles of transporting the electron generated in the photoelectric conversion layer to the electrode film and blocking the positive hole from moving from the electrode film which is the destination of the electron to the photoelectric conversion layer. The positive hole transport layer has the roles of transporting the positive hole generated from the photoelectric conversion layer to the electrode film and blocking the electron from moving from the electrode film which is the destination of the positive hole to the photoelectric conversion layer. The electron block layer has the roles of preventing the electron from moving from the electrode film to the photoelectric conversion layer, preventing the recombination in the photoelectric conversion layer, and decreasing the dark current. The positive hole block layer has the functions of preventing the positive hole from moving from the electrode film to the photoelectric conversion layer, preventing the recombination in the photoelectric conversion layer, and decreasing the dark current.

The positive hole block layer is formed by laminating alone or two or more positive hole blocking substance or mixing two or more positive hole blocking substance. The positive hole blocking substance is not limited as long as the compound can block the positive hole from flowing out from the electrode to the outside of the element. Examples of the compound capable of using for the positive hole block layer include phenanthroline derivative such as bathophenanthroline and bathocuproine, silole derivative, quinolinol derivative metal complex, oxadiazole derivative, oxazole derivative, quinoline derivative, and one or two or more these compounds can be used.

The typical element structure of the organic photoelectric conversion element of the present invention is shown in FIG. 3, but the present invention is not limited to the structure. In the embodiment example of FIG. 3, 1 represents the insulation part, 2 represents the one electrode film, 3 represents the electron block layer, 4 represents the photoelectric conversion layer, 5 represents the positive hole block layer, 6 represents the other electrode film, 7 represents the insulation base material or another photoelectric conversion element respectively. The reading transistor is not drawn in the figure but may be connected to the electrode film of 2 or 6. In addition when the photoelectric conversion layer 4 is transparent, the reading transistor also may be formed as the film outside of the electrode film on opposite side of the light incident side. The light may be received from either of above or below the photoelectric conversion element unless the components except for the photoelectric conversion layer 4 prevent the light having the main absorption wavelength of the photoelectric conversion layer from coming in extremely.

EXAMPLES

The present invention will be explained in more detail with the Examples hereinafter, but is not limit to these Examples. Note that in the Examples the "part" means "part by mass" and "%" means "% by mass" respectively unless specified otherwise. "M" means the molar concentration. The reaction temperature is a temperature within the reaction system, unless otherwise noted.

In Examples, EI-MS was measured by ISQ7000 manufactured by Thermo Fisher Scientific K. K. The thermal analytical measuring was performed by TGA/DSC1 manufactured by Mettler Toledo International. Inc. Nuclear magnetic resonance (NMR) was measured by JNM-EC400 manufactured by Japan Electron Optics Laboratory Ltd.

The mobility of the field-effect transistor was evaluated by using B1500 or 4155C manufactured by Agilent Technologies, Inc. which are the semiconductor parameter for evaluating the mobility. The surface of the organic thin film was observed by using the atomic force microscope (hereinafter AFM) AFM5400L manufactured by Hitachi High-Technologies Corporation.

In Examples, the current measurement under the voltage application of the organic photoelectric conversion element was performed by using the semiconductor parameter analyzer 4200-SCS (manufactured by Keithley Instruments K. K.). The incident light was irradiated by PVL-3300 (manufactured by Asahi Spectra Co., Ltd.) with half value width of 20 nm. In Examples the bright and dark electric current ratio means the number obtained by dividing the current value when the irradiation is performed by the current value in the dark.

Example 1 (Synthesis of the Fused Polycyclic Aromatic Compound Represented by No. 1 of Concrete Examples)

DMF (140 parts), water (4 parts), the compound represented by following formula 1 synthesized by the method according to the description in JP 2009-196975 A (1.6 parts), 4-(p-terphenyl) boronic acid (0.96 parts), tripotassium phosphate (1.24 parts), and tetrakis(triphenyl phosphine)palladium (0) (0.34 parts) were mixed and stirred under a nitrogen atmosphere at 80° C. for 9 hours. After the reaction solution obtained was cooled to the room temperature, water (150 parts) was added and the solid content was separated out by filtration. After the solid content obtained was washed with acetone and DMF and dried, the compound represented by No. 1 of the concrete examples (1.0 parts, yield 63%) was obtained by performing the sublimation to purify.

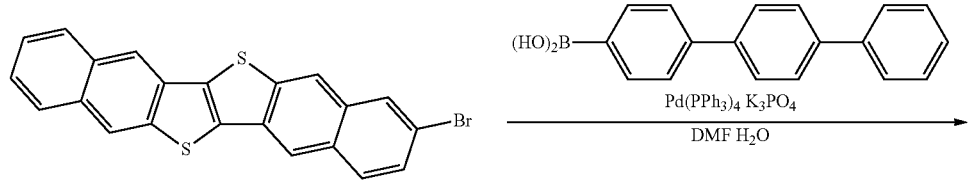

1

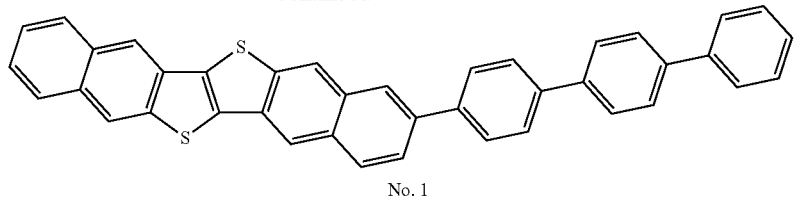

No. 1

The results of the EI-MS spectrum measurement and the thermal analytical measuring of the compound represented by No. 1 of the concrete examples obtained in Example 1 were as follows.

EI-MS m/z: Calculated for $C_{40}H_{24}S_2[M^+]$: 568.13. Found: 568.23

Thermal Analysis (Heat Absorption Peak): 509.4° C. (Under Nitrogen Atmosphere Condition)

Example 2 (Synthesis of the Fused Polycyclic Aromatic Compound Represented by No. 2 of Concrete Examples)

(Step 1) the Synthesis of the Intermediate Compound Represented by Following Formula 2

DMF (400 parts), water (10 parts), 4-(1-naphthyl)phenyl boronic acid (12.0 parts), 1-bromo-4-iodobenzene (13.7 parts), potassium phosphate (61.6 parts), and tetrakis(triphenyl phosphine)palladium (0) (1.7 parts) were mixed and stirred under a nitrogen atmosphere at 80° C. for 10 hours. After the reaction solution obtained was cooled to the room temperature, water (1000 parts) was added and the solid content was separated out by filtration. The solid obtained was washed with methanol and dried to obtain the intermediate compound represented by following formula 2 (17.1 parts, yield 98%) in the form of white sold.

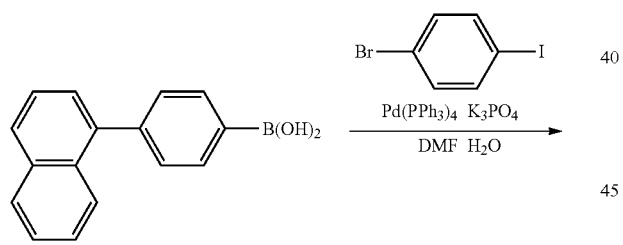

2

(Step 2) the Synthesis of the Intermediate Compound Represented by Following Formula 3

Toluene (250 parts), the intermediate compound represented by formula 2 obtained in Step 1 (8.5 parts), bis(pinacolato)diboron (7.2 parts), potassium acetate (4.6 parts), and [1,1'-bis(diphenylphosphino)ferrocene]dichloropalladium(II) dichloromethane adduct (0.6 parts) were mixed and stirred under nitrogen atmosphere at the reflux temperature for 6 hours. After the reaction solution was cooled to the room temperature, the solid content was separated out by filtration and the solvent was removed under reduced pressure. The solid obtained was purified by silica gel column chromatography (developing solvent; toluene: hexane=1:1) and further recrystallization was performed in ethyl acetate to obtain the intermediate compound represented by following formula 3 (2.2 parts, yield 23%) in the form of white solid.

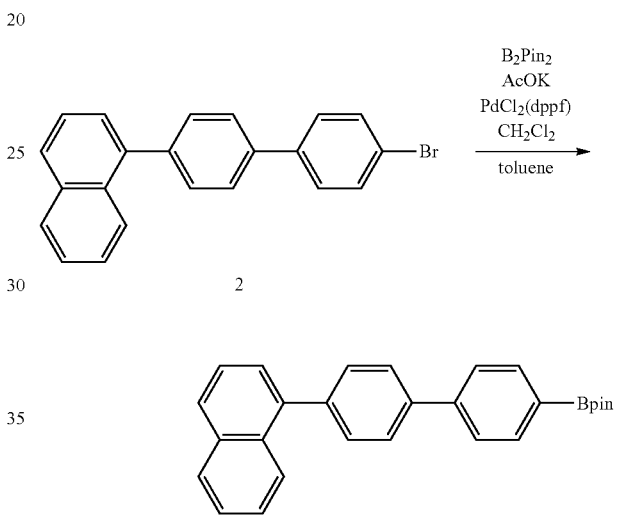

The results of the nuclear magnetic resonance measurement of the intermediate compound represented by formula 3 obtained in Step 2 were as follows.

$^1$H-NMR (CDCl$_3$): 7.96 (d, 1H), 7.93-7.90 (m, 3H), 7.87 (d, 1H), 7.75 (d, 2H), 7.70 (d, 2H), 7.58-7.42 (m, 6H), 1.37 (s, 12H)

(Step 3) the Synthesis of the Aromatic Compound Represented by No. 2 of the Concrete Examples DMF (200 parts), water (5 parts), the compound represented by above formula 1 synthesized by the method according to the description in JP 2009-196975 A (1.5 parts), the intermediate compound represented by formula 3 obtained in Step 2 (1.7 parts), potassium phosphate (1.5 parts), and tetrakis(triphenyl phosphine)palladium (0) (0.4 parts) were mixed and stirred under nitrogen atmosphere at 80° C. for 6 hours. After the reaction solution obtained was cooled to the room temperature, water (200 parts) was added and the solid content was separated out by filtration. After the solid obtained was washed with acetone and DMF and dried, the compound represented by No. 2 of the concrete examples (1.0 parts, yield 44%) was obtained by performing the sublimation to purify.

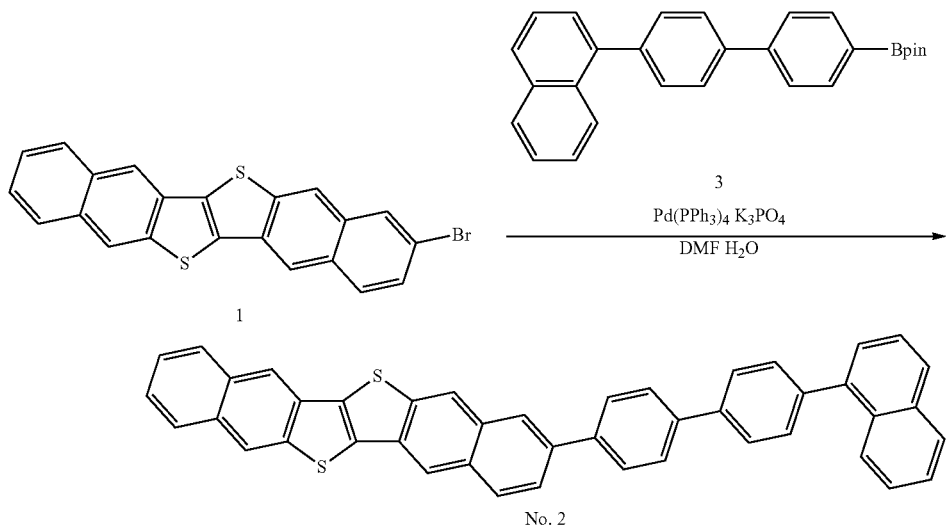

The results of the EI-MS spectrum measurement and the thermal analytical measuring of the compound represented by No. 2 of the concrete examples obtained in Example 2 were as follows.

EI-MS m/z: Calculated for $C_{44}H_{26}S_2[M^+]$: 618.15. Found: 618.36

Thermal Analysis (Heat Absorption Peak): 435.1° C. (Under Nitrogen Atmosphere Condition)

Example 3 (Manufacture of Field-Effect Transistor 1 of Present Invention)

On the n-doped silicon wafer with Si thermal oxide film subjected to the surface treatment with 1,1,1,3,3,3-hexamethyldisilazane, the fused polycyclic aromatic compound represented by No. 1 of the concrete examples obtained in Example 1 was formed as the film having the thickness of 50 nm by resistant heating type vacuum vapor deposition. Next on the organic thin film obtained above Au was vacuum vapor deposited by using the shadow mask to manufacture the source electrode and the drain electrode with the channel length of 20 to 200 μm and the channel width of 2000 μm, respectively. The top contact type field-effect transistor element 1 (FIG. 1B) of the present invention was manufactured. Note that in the field-effect transistor element 1, the thermal oxide film of the n-doped silicon wafer with thermal oxide film has the function of the insulator layer, and the n-doped silicon wafer has both functions of the substrate and the gate electrode.

Comparative Example 1 (Manufacture of Field-Effect Transistor 2 for Comparison)

The field-effect transistor element 2 for comparison was manufactured by the method according to Example 3 except for that the fused polycyclic aromatic compound represented by No. 1 of the concrete examples obtained in Example 1 was replaced by the compound represented by following formula (R) synthesized according to the description in JP 5,674,916 B.

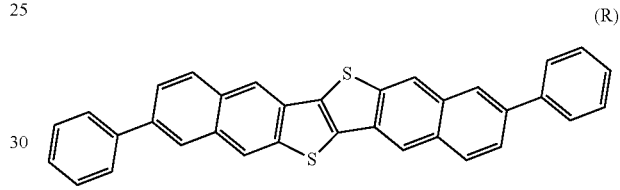

(R)

(Heat Resistance Test of Field-Effect Transistor Elements 1 and 2)

The performance of the field-effect transistor depends on the current amount flowing when the electric potential is applied between the source electrode and the drain electrode in the condition where the electric potential is applied to the gate. By using the results of measuring the current value into the following formula (a) representing the electric characteristics of the carrier type generated in the organic semiconductor layer, the mobility can be calculated.

$$Id = Z\mu Ci(Vg-Vt)^2/2L \tag{a}$$

In formula (a), Id is a saturated source-drain current value, Z is a channel width, Ci is an electric capacity of insulator, Vg is a gate voltage, Vt is a threshold voltage, L is a channel length, and μ is a mobility (cm²/Vs) determined. Ci is determined by a dielectric constant of $SiO_2$ insulator film used, Z and L are determined by a device structure of the organic transistor device, Id and Vg are determined when measuring a current value of the field-effect transistor device, and Vt can be obtained by Id and Vg. By substituting each value into formula (a), the mobility at each gate voltage can be calculated.

On one substrate, four field-effect transistor elements 1 and 2 were manufactured, respectively, by the method according to Example 3 and Comparative Example 1. After heating the field-effect transistor elements 1 and 2 at 120° C. for 30 minutes under air pressure, the carrier mobility μ was measured by the method aforementioned. Next, after further heating at 150° C. for 30 minutes under air pressure the field-effect transistor elements 1 and 2 subjected to the measurement of the carrier mobility/I after heating at 120° C. aforementioned, the carrier mobility μ was measured by the method aforementioned. Finally, after further heating at 1800° C. for 30 minutes under air pressure the field-effect transistor elements 1 and 2 subjected to the measurement of the carrier mobility/I after heating at 1500° C. aforementioned, the carrier mobility μ was measured by the method aforementioned. Note that the evaluation criteria for the heat resistance is as follows. The results were shown in Table 1.

Evaluation Criteria

A: The rate of change of the mobility after heating based on the mobility just after manufacturing the field-effect transistor is less than 30%.

B: The rate of change of the mobility after heating based on the mobility just after manufacturing the field-effect transistor is equal to or more than 30%.

C: The field-effect transistor element was broken by heating and the evaluation is impossible.

TABLE 1

1 Results of heat resistance test of field-effect transistor (FET) element

| Element | Heat conditions | | |
| --- | --- | --- | --- |
|  | 120° C. for 30 minutes | 150° C. for 30 minutes | 180° C. for 30 minutes |
| FET element 1 (Example) | A | A | A |
| FET element 2 (Comparative Example) | A | A | C |

(Heat Resistance Test of Organic Thin Film)

On the n-doped silicon wafer with Si thermal oxide film subjected to the surface treatment with 1,1,1,3,3,3-hexamethyldisilazane, the fused polycyclic aromatic compound represented by No. 1 of the concrete examples obtained in Example 1 and the compound represented by formula (R) used in Comparative Example 1 were formed as the organic thin film having a thickness of 50 nm by the vapor deposition method described in Example 3 respectively. After heating the organic thin films obtained above at 120° C. for 30 minutes under air pressure, the organic thin films were cooled to the room temperature temporarily. Next, after heating the organic thin films at 150° C. for 30 minutes under air pressure, the organic thin films were cooled to the room temperature temporarily. After heating the organic thin film at 180° C. for 30 minutes under air pressure yet again, the organic thin films were cooled to the room temperature and the value of the surface roughness (Sa) just after manufacturing the organic thin film, and the values of the surface roughness (Sa) after heating at 120° C., 150° C., and 180° C. were calculated by using the AFM analysis program. The results were shown in Table 2.

The surface state of the organic thin film for calculating the value of the surface roughness used above was observed by AFM (scanning range: 1 μm). The AFM image of the organic thin film containing the fused polycyclic aromatic compound represented by No. 1 of the concrete examples was shown in FIG. 4 and the AFM image of the organic thin film containing the compound represented by formula (R) was shown in FIG. 5, respectively.

TABLE 2

2 Results of heat resistance test (surface roughness (Sa))

| Compound | Immediately after film formation | 180° C. for 30 minutes |
| --- | --- | --- |
| No. 1 | 1.7 nm | 14.5 nm |
| Formula (R) | 6.0 nm | 75.1 nm |

From the results in Table 1, it is clear that the field-effect transistor of the present invention has more excellent heat resistance than the field-effect transistor for comparison.

In addition, the results in Table 2 reveal that the change of the surface roughness of the organic thin film containing the fused polycyclic aromatic compound represented by No. 1 of the concrete examples of the present invention before and after the heating test is smaller than the organic thin film containing the compound represented by formula (R) for comparison. The comparison of the image observed by AFM shown in FIG. 4 of the organic thin film containing the fused polycyclic aromatic compound represented by No. 1 of the concrete examples and the image observed by AFM shown in FIG. 5 of the organic thin film containing the compound represented by formula (R) for comparison shows it clearly.

Example 4 (Manufacture of Field-Effect Transistor 3 of the Present Invention)

The field-effect transistor element 3 was manufactured by the method according to Example 3 except for that the fused polycyclic aromatic compound represented by No. 1 of the concrete examples obtained in Example 1 was replaced with the fused polycyclic aromatic compound represented by No. 2 of the concrete examples.

(Heat Resistance Test of Field-Effect Transistor Element 3)

The heat resistance test of the field-effect transistor element 3 was performed by the same method as the method for the field-effect transistor elements 1 and 2. The result was shown in Table. 3.

TABLE 3

3 Results of heat resistance test of field-effect transistor (FET) element

| Element | Heat conditions | | |
| --- | --- | --- | --- |
|  | 120° C. for 30 minutes | 150° C. for 30 minutes | 180° C. for 30 minutes |
| FET element 3 (Example) | B | B | B |

(Heat Resistance Test of Organic Thin Film)

The heat resistance test of the organic thin film formed by using the fused polycyclic aromatic compound represented by No. 2 of the concrete examples obtained in Example 2 was performed by the same method as the method for the organic thin film formed by using the fused polycyclic aromatic compound represented by No. 1 of the concrete examples and the compound represented by formula (R) used for Comparative Example 1. The results were shown in Table 4.

The surface state of the organic thin film for calculating the surface roughness used above was observed by AFM (scanning range: 1 μm) The AFM image of the organic thin film containing the fused polycyclic aromatic compound represented by No. 2 of the concrete examples was shown in FIG. 6.

TABLE 4

| | 4 Results of heat resistance test (surface roughness (Sa)) | |
|---|---|---|
| Compound | Immediately after film formation | 180° C. for 30 minutes |
| No. 2 | 2.2 nm | 6.5 nm |

From the results in Table 3, it is clear that the field-effect transistor of the present invention has more excellent heat resistance than the field-effect transistor for comparison.

In addition, the results in Table 4 reveal that the change of the surface roughness of the organic thin film containing the fused polycyclic aromatic compound of the present invention represented by No. 2 of the concrete examples before and after heating test is smaller than the organic thin film containing the compound represented by formula (R) for comparison. The comparison of the image observed by AFM shown in FIG. 6 of the organic thin film containing the fused polycyclic aromatic compound represented by No. 2 of the concrete examples and the image shown observed by AFM in FIG. 5 of the organic thin film comprising the compound represented by formula (R) for comparison shows it clearly.

Example 5 (Synthesis of Fused Polycyclic Aromatic Compound Represented by No. 3 of Concrete Examples)

(Step 4) the Synthesis of the Intermediate Compound Represented by the Following Formula 4

DMF (210 parts), 4-(p-terphenyl) boronic acid (8.64 parts), 1-bromo-4-iodobenzene (8.49 parts), 2 M sodium carbonate solution (45.0 parts), and tetrakis(triphenyl phosphine)palladium (0) (0.69 parts) were mixed and stirred under nitrogen atmosphere at 80° C. for 7 hours. After the reaction solution obtained was cooled to the room temperature, water (200 parts) was added and the solid content was separated out by filtration. The solid obtained was washed with methanol, next with in the order DMF, acetone and dried to obtain the intermediate compound represented by the following formula 4 (9.55 parts, yield 83%) in the form of white sold.

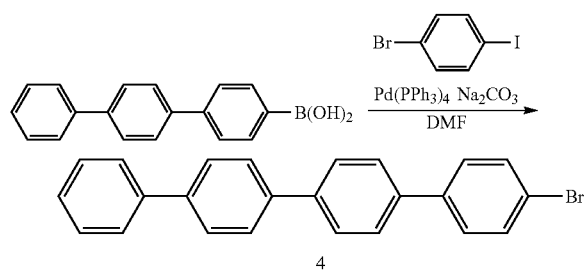

(Step 5) the Synthesis of the Intermediate Compound Represented by the Following Formula 5

Toluene (80 parts), the intermediate compound represented by formula 4 obtained in Step 4 (3.08 parts), bis (pinacolato)diboron (2.44 parts), potassium acetate (2.36 parts), and [1,1'-bis(diphenylphosphino)ferrocene]dichloropalladium(II) dedichloromethane adduct (0.26 parts) were mixed and stirred under nitrogen atmosphere at the reflux temperature for 8 hours. After the reaction solution obtained was cooled to the room temperature, the reaction solution was purified by silica gel column chromatography (developing solvent chloroform) and further recrystallized in toluene to obtain the intermediate compound represented by the following formula 5 (2.75 parts, yield 79%) in the form of white solid.

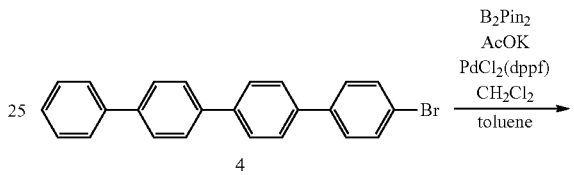

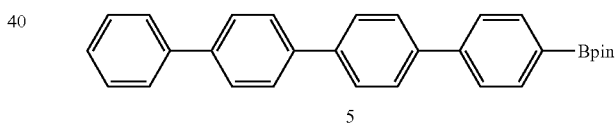

(Step 6) the Synthesis of the Aromatic Compound Represented by No. 3 of the Concrete Examples DMF (80 parts), the compound represented by above formula 1 synthesized by the method according to the description in JP 2009-196975 A (1.68 parts), the intermediate compound represented by formula 5 obtained in Step 5 (2.59 parts), 2 M potassium phosphate (6.0 parts), palladium acetate (0.09 parts) and 2-dicyclohexylphosphino-2', 6'-dimethoxybiphenyl(SPhos) (0.33 parts) were mixed and stirred under nitrogen atmosphere at 80° C. for 4 hours. After the reaction solution obtained was cooled to the room temperature, water (100 parts) was added and the solid content was separated out by filtration. After the solid content obtained was washed with acetone and DMF and dried, the compound represented by No. 3 of the concrete examples (1.73 parts, yield 67%) was obtained by performing the sublimation to purify.

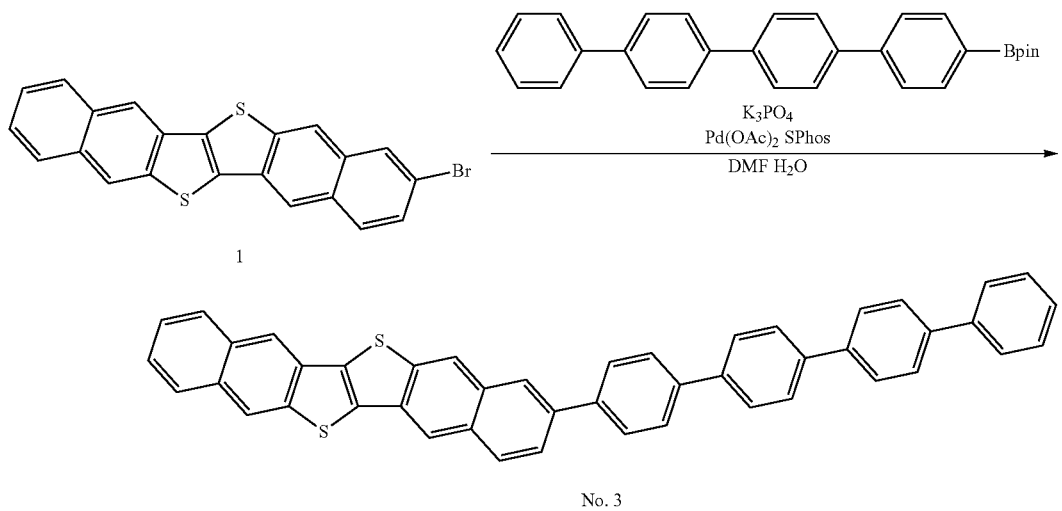

No. 3

The results of the EI-MS spectrum measurement and the thermal analytical measuring of the compound represented by No. 3 of the concrete examples obtained in Example 5 were as follows.
EI-MS m/z: Calculated for $C_{46}H_{28}S_2$ [M$^+$]: 644.85. Found: 644.46
Thermal Analytical Measuring (Heat Absorption Peak): 527.6° C. (Under a Nitrogen Atmosphere Condition)

Example 6 (Manufacture of Field-Effect Transistor 4 of Present Invention)

The field-effect transistor element 4 was manufactured by the method according to Example 3 except for that the fused polycyclic aromatic compound represented by No. 1 of the concrete examples obtained in Example 1 was replaced with the fused polycyclic aromatic compound represented by No. 3 of the concrete examples.
(Heat Resistance Test of Field-Effect Transistor Element 4)
The heat resistance test of the field-effect transistor element 4 was performed by the same method as the method for the field-effect transistor elements 1 and 2. The results were shown in Table 5.

TABLE 5

5 Results of heat resistance test of field-effect transistor (FET) element

| Element | Heat conditions | | |
|---|---|---|---|
| | 120° C. for 30 minutes | 150° C. for 30 minutes | 180° C. for 30 minutes |
| FET element 4 (Example) | A | A | A |

(Heat Resistance Test of Organic Thin Film)
The heat resistance test of the organic thin film formed by using the fused polycyclic aromatic compound represented by No. 3 of the concrete examples obtained in Example 5 was performed by the same method as the method for the organic thin film formed by using the fused polycyclic aromatic compound represented by No. 1 of the concrete examples and the compound represented by formula (R) used for Comparative Example 1. The results were shown in Table 6.

The surface state of the organic thin film for calculating the surface roughness used above was observed by AFM (scanning range: 1 μm) The AFM image of the organic thin film containing the fused polycyclic aromatic compound represented by No. 3 of the concrete examples was shown in FIG. 7.

TABLE 6

6 Results of heat resistance test (surface roughness (Sa))

| Compound | Immediately after film formation | 180° C. for 30 minutes |
|---|---|---|
| No. 3 | 2.8 nm | 3.4 nm |

From the results in Table 5, it is clear that the field-effect transistor of the present invention has more excellent heat resistance than the field-effect transistor for comparison.
In addition, the results in Table 6 reveal that the change of the surface roughness of the organic thin film containing the fused polycyclic aromatic compound represented by No. 3 of the concrete examples before and after heating test is smaller than the organic thin film containing the compound represented by formula (R) for comparison. The comparison of the image observed by AFM shown in FIG. 7 of the organic thin film containing the fused polycyclic aromatic compound represented by No. 3 of the concrete examples and the image shown observed by AFM in FIG. 5 of the organic thin film containing the compound represented by formula (R) for comparison shows it clearly.

Example 7 (Manufacture and Evaluation of Organic Photoelectric Conversion Element 1 of Compound Represented by No. 1 of Concrete Examples Obtained in Example 1)

On the ITO transparent conductive glass (manufactured by GEOMATEC Co., Ltd. the film thickness of ITO 150 nm), the fused polycyclic aromatic compound represented by No. 1 of the concrete examples obtained in Example 1 was formed as a film having a film thickness of 100 nm by the resistant heating type vacuum vapor deposition. Next, the organic photoelectric conversion element 1 of the present invention was manufactured by forming the film having a thickness of 100 nm from aluminum as an electrode by the vacuum film deposition. When the voltage of 3 V was applied to the ITO and aluminum as the electrode and the light irradiation was performed with the light having a wavelength of 450 nm, the bright and dark electric current ratio was 250000.

Example 8 (Manufacture and Evaluation of Organic Photoelectric Conversion Element 2 of Compound Represented by No. 2 of Concrete Examples Obtained in Example 2)

The organic photoelectric conversion element 2 was manufactured by the method according to Example 7 except for that the fused polycyclic aromatic compound represented by No. 1 of the concrete examples obtained in Example 1 was replaced with the fused polycyclic aromatic compound represented by No. 2 of the concrete examples obtained in Example 2. When the voltage of 3 V was applied to the ITO and aluminum as an electrode and the light irradiation was performed with the light having a wavelength of 450 nm, the bright and dark electric current ratio was 6000.

Example 9 (Manufacture and Evaluation of Organic Photoelectric Conversion Element 3 of Compound Represented by No. 3 of Concrete Examples Obtained in Example 5)

The organic photoelectric conversion element 3 was manufactured by the method according to Example 7 except for that the fused polycyclic aromatic compound represented by No. 1 of the concrete examples obtained in Example 1 was replaced with the fused polycyclic aromatic compound represented by No. 3 of the concrete examples obtained in Example 5. When the voltage of 3 V was applied to the ITO and aluminum as an electrode and the light irradiation was performed with the light having a wavelength of 450 nm, the bright and dark electric current ratio was 15000.

Comparative Example 2 (Manufacture and Evaluation of Organic Photoelectric Conversion Element 4 for Comparison)

The organic photoelectric conversion element 4 for comparison was manufactured by the method according to Example 7 except for that the fused polycyclic aromatic compound represented by No. 1 of the concrete examples obtained in Example 1 was replaced with the compound represented by the following formula (DNTT) synthesized according to the description in JP 4,958,119 B. When the voltage of 3 V was applied to the ITO and aluminum as an electrode and the light irradiation was performed with the light having a wavelength of 450 nm, the bright and dark electric current ratio was 4.

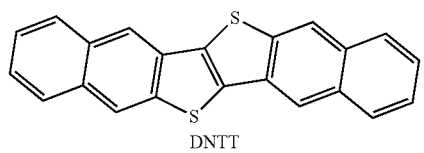

DNTT

Comparative Example 3 (Synthesis of the Fused Polycyclic Aromatic Compound Represented by the Following Formula (R2))

DMF (50 parts), the compound represented by above formula 1 synthesized by the method according to the description in JP 2009-196975 A (1.0 parts), 4-biphenylboronic acid (0.94 parts), tripotassium phosphate (1.0 parts), palladium acetate (0.03 parts), and 2-dicyclohexylphosphyno-2',6'-dimethoxybiphenyl(SPhos) (0.10 parts) were mixed and stirred under nitrogen atmosphere at 80° C. for 6 hours. After the reaction solution obtained was cooled to the room temperature, water (50 parts) was added and the solid content was separated out by filtration. After the solid obtained was washed with acetone and DMF and dried, the compound represented by the following formula (R2) (0.7 parts, yield 60%) was obtained by performing the sublimation to purify.

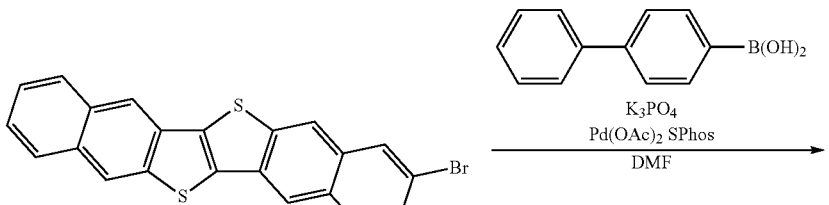

1

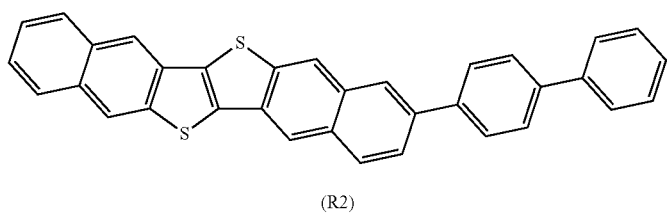

(R2)

The results of the EI-MS spectrum measurement and the thermal analytical measuring of the compound represented by above formula (R2) obtained in Comparative Example 3 were as follows.

EI-MS m/z: Calculated for $C_{34}H_{20}S_2$ [M+]: 492.10. Found: 492.44

Thermal Analytical Measuring (Heat Absorption Peak): 465.9° C. (Under Nitrogen Atmosphere Condition)

Comparative Example 4 (Manufacture of Field-Effect Transistor Element 5 for Comparison)

The field-effect transistor element 5 was manufactured by the method according to Example 3 except for that the fused polycyclic aromatic compound represented by No. 1 of the concrete examples obtained in Example 1 was replaced with the fused polycyclic aromatic compound represented by the above formula (R2) in Comparative Example 3.

(Heat Resistance Test of Field-Effect Transistor Element 5)

The heat resistance test of the field-effect transistor element 5 was performed by the same method as the method for the field-effect transistor elements 1 to 4. The results were shown in Table 7.

TABLE 7

7 Results of heat resistance test of field-effect transistor (FET) element

| | Heat conditions | | |
|---|---|---|---|
| Element | 120° C. for 30 minutes | 150° C. for 30 minutes | 180° C. for 30 minutes |
| FET element 5 (Example) | A | B | C |

(Heat Resistance Test of Organic Thin Film)

The heat resistance test of the organic thin film formed by using the fused polycyclic aromatic compound represented by above formula (R2) in the Comparative Example 3 was performed by the same method as the method for the organic thin film formed by using the fused polycyclic aromatic compound represented by No. 1 and No. 3 of the concrete examples and the compound represented by formula (R) used in Comparative Example 1. The results were shown in Table 8.

The surface state of the organic thin film for calculating the surface roughness used above was observed by AFM (scanning range: 1 μm) The AFM image of the organic thin film containing the fused polycyclic aromatic compound represented by formula (R2) in the Comparative Example 3 was shown in FIG. 8.

TABLE 8

8 Results of heat resistance test (surface roughness (Sa))

| Compound | Immediately after film formation | 180° C. for 30 minutes |
|---|---|---|
| R2 | 7.3 nm | 142.7 nm |

From the results in Table 7, it is clear that the field-effect transistor of the present invention has more excellent heat resistance than the field-effect transistor for comparison.

In addition, the results in Table 8 reveal that the change of the surface roughness of the organic thin film containing the fused polycyclic aromatic compound of the present invention before and after heating test is smaller than the organic thin film containing the compound represented by formula (R) and (R2) for comparison. The comparison of the image observed by AFM shown in FIGS. 4, 6, and 7 of the organic thin film containing the fused polycyclic aromatic compound of the present invention and the image observed by AFM shown in FIG. 8 of the organic thin film containing the compound represented by formula (R2) for comparison shows it clearly.

Example 10 (Synthesis of Fused Polycyclic Aromatic Compound Represented by No. 29 of Concrete Examples)

(Step 7) the Synthesis of the Intermediate Compound Represented by the Following Formula 6

DMF (2300 parts) 2-bromo-6-methoxynaphthalene (70.5 parts), 4-biphenylboronic acid (96.6 parts), tripotassium phosphate (126.9 parts), and tetrakis(triphenyl phosphine) palladium (0) (13.6 parts) were mixed and stirred under nitrogen atmosphere at 70° C. for 5 hours. After the reaction solution obtained was cooled to the room temperature, water was added and the solid produced was separated out by filtration. The solid obtained was washed with methanol and dried to obtain the intermediate compound represented by the following formula 6 (91.2 parts, yield 99%) in the form of white sold.

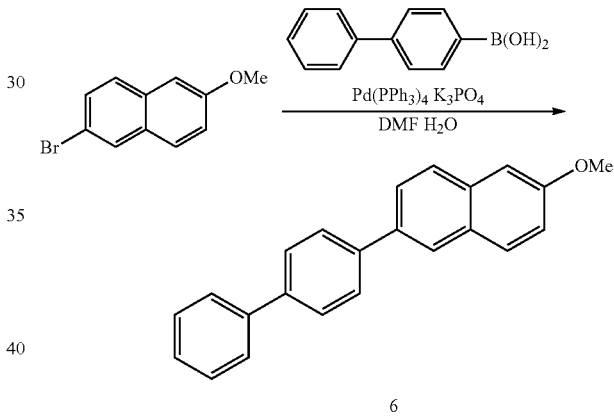

6

(Step 8) the Synthesis of the Intermediate Compound Represented by the Following Formula 7

The intermediate compound represented by formula 6 obtained in Step 7 (70.0 parts) and pyridine hydrochloride (259.0 parts) were mixed and stirred under nitrogen atmosphere at 180° C. for 3 hours. After the reaction solution obtained was cooled to the room temperature, water was added and the solid obtained was separated out by filtration. The solid filtrated was washed with methanol and next with ethyl acetate and dried to obtain the intermediate compound represented by the following formula 7 (57.0 parts, yield 86%) in the form of white sold.

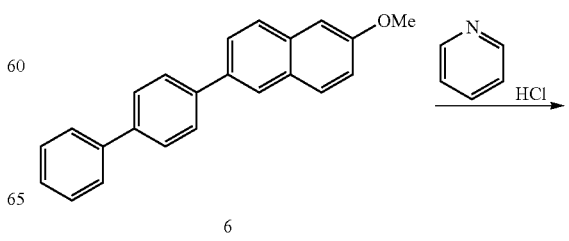

6

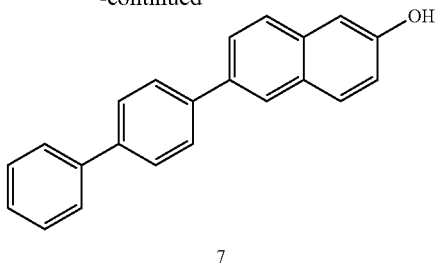

7

(Step 9) the Synthesis of the Intermediate Compound Represented by the Following Formula 8

Chloroform (2000 parts), the intermediate compound represented by formula 7 obtained in Step 8 (15.0 parts) and triethylamine (41.0 parts) were mixed. After the mixture was heated to 50° C., trifluoromethane sulfonic acid anhydride (85.6 parts) was dropped under nitrogen atmosphere. After dropping, the mixture was heated to 60° C. and stirred for 30 minutes. After the reaction solution obtained was cooled to the room temperature and water (500 parts) was added, the organic layer was separated and the solvent was removed under reduced pressure. The solid obtained was washed with acetone and dried to obtain the intermediate compound represented by the following formula 8 (19.2 parts, yield 88%).

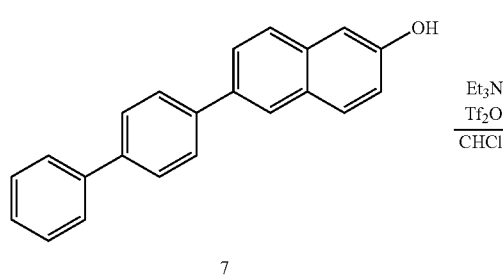

(Step 10) the Synthesis of the Intermediate Compound Represented by the Following Formula 9

Toluene (530 parts), the intermediate compound represented by formula 8 obtained in Step 9 (18.7 parts), bis(pinacolato)diboron (13.3 parts), potassium acetate (8.6 parts), and [1,1'-bis(diphenylphosphino)ferrocene]dichloropalladium(II) dichloromethane adduct (1.1 parts) were mixed and stirred under nitrogen atmosphere at the reflux temperature for 7 hours. The reaction solution obtained was cooled to the room temperature and the solid content was separated by filtration. The filtrate containing the product was obtained. Next, the filtrate was purified by silica gel column chromatography (developing solvent; toluene) and the solvent was distilled off under the reduced pressure to obtain the white solid. The white solid obtained was recrystallized in toluene to obtain the intermediate compound represented by the following formula 9 (5.3 parts, yield 30%).

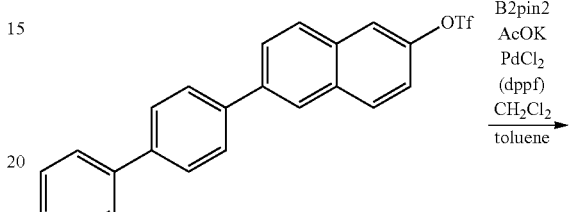

8

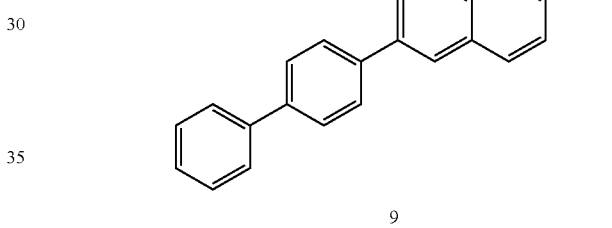

9

The results of the nuclear magnetic resonance measurement of the intermediate compound represented by formula 9 obtained in Step 10 were as follows.

$^1$H-NMR (DMSO-d6): 8.34 (d, 1H), 8.29 (d, 1H), 8.13 (d, 1H), 7.95-7.91 (m, 3H), 7.83-7.72 (m, 6H), 7.52-7.36 (m, 3H), 1.34 (s, 12H)

(Step 11) the Synthesis of the Aromatic Compound Represented by No. 29 of the Concrete Examples DMF (250 parts), the compound represented by above formula 1 synthesized by the method according to the description in JP 2009-196975 A (2.5 parts), the intermediate compound represented by formula 9 obtained in Step 10 (4.0 parts), potassium phosphate (2.5 parts), palladium acetate (0.10 parts) and 2-dicyclohexylphosphino-2',6'-dimethoxybiphenyl(SPhos) (0.70 parts) were mixed and stirred under nitrogen atmosphere at 80° C. for 5 hours. After the reaction solution obtained was cooled to the room temperature, water (250 parts) was added and the solid content was separated out by filtration. After the solid obtained was washed with acetone and DMF and dried, the compound represented by No. 29 of the concrete examples (2.7 parts, yield 74%) was obtained by performing the sublimation to purify.

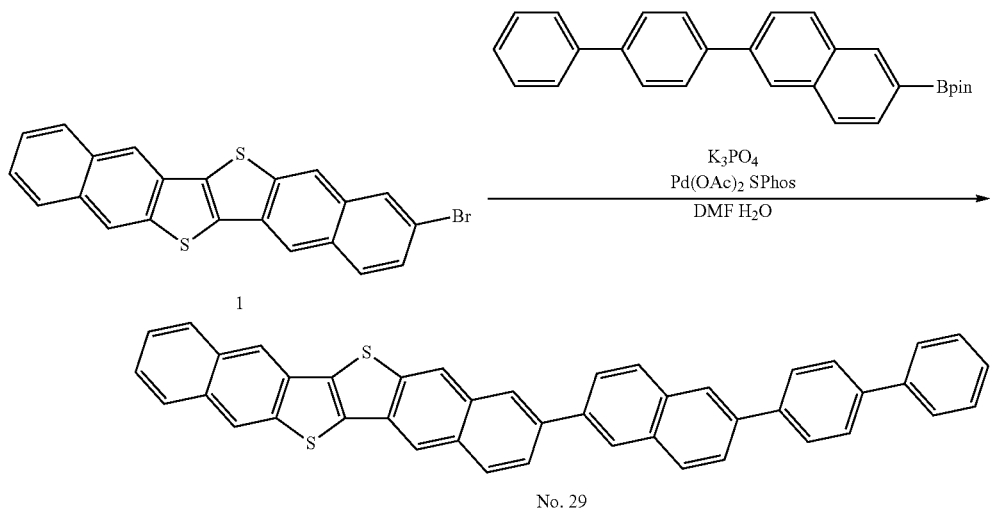

No. 29

The results of the EI-MS spectrum measurement and the thermal analytical measuring of the compound represented by No. 29 of the concrete examples obtained in Example 10 were as follows.

EI-MS m/z: Calculated for $C_{44}H_{26}S_2[M^+]$: 618.15. Found: 618.40 Thermal analytical measuring (heat absorption peak): 501.0° C. (under nitrogen atmosphere conditions)

Example 11 (Synthesis of Fused Polycyclic Aromatic Compound Represented by No. 30 of Concrete Examples)

(Step 12) the Synthesis of the Intermediate Compound Represented by the Following Formula 10

DMF (250 parts), 2-bromo-6-methoxynaphthalene (11.5 parts), 2-naphthylboronic acid (10.0 parts), tripotassium phosphate (20.6 parts), and tetrakis(triphenyl phosphine) palladium (0) (1.7 parts) were mixed and stirred under a nitrogen atmosphere at 90° C. for 5 hours. After the reaction solution obtained was cooled to the room temperature, water was added and the solid produced was taken out by filtration. The solid obtained was washed with methanol and dried to obtain the intermediate compound represented by the following formula 10 (13.5 parts, yield 98%)

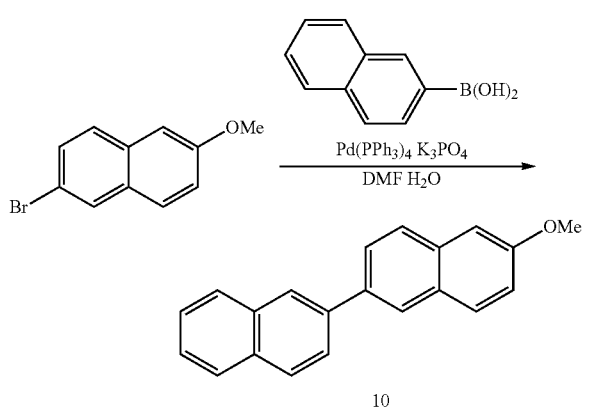

10

(Step 13) the Synthesis of the Intermediate Compound Represented by the Following Formula 11

The intermediate compound represented by formula 10 obtained in Step 12 (13.0 parts) and pyridine hydrochloride (53 parts) were mixed and stirred under nitrogen atmosphere at 180° C. for 5 hours. After the reaction solution obtained was cooled to the room temperature, ethyl acetate and water were added to separate into two liquids. The solvent was distilled off under the reduced pressure to obtain the intermediate compound represented by the following formula 11 (11.5 parts, yield 94%)

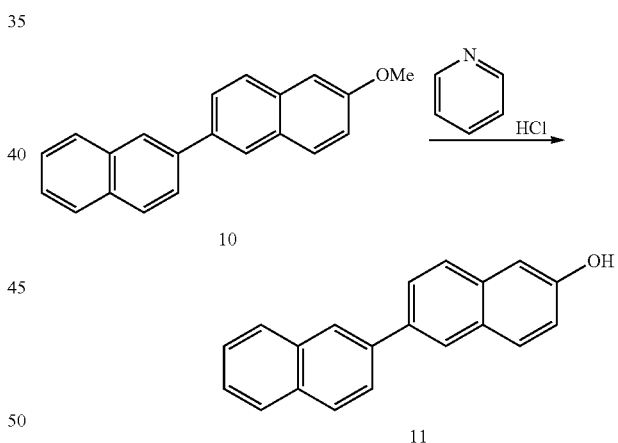

11

(Step 14) the Synthesis of the Intermediate Compound Represented by the Following Formula 12

After the intermediate compound represented by formula 11 obtained in Step 13 (11.5 parts) was added to the mixed solution of dichloromethane (150 parts) and triethylamine (8.6 parts) and cooled to 0° C., trifluoromethane sulfonic acid anhydride (14.4 parts) was dropped slowly. After dropping, the mixture was heated to 25° C. and stirred for 2 hours. Water and toluene were added to the reaction solution obtained to separate into two liquids and the solvent was distilled off under reduced pressure to obtain the brown solid. The solid was suspended in methanol (100 parts). The filtration was performed to obtain the intermediate compound represented by the following formula 12 (15.2 parts, yield 89%) in the form of white solid.

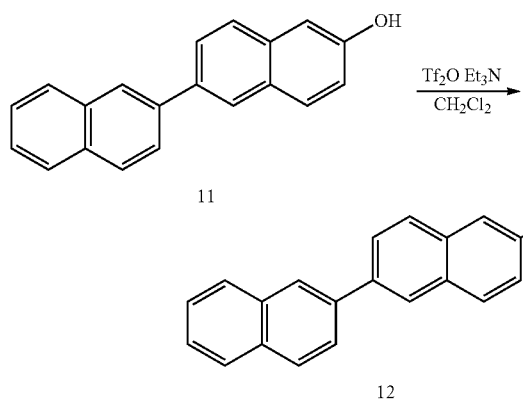
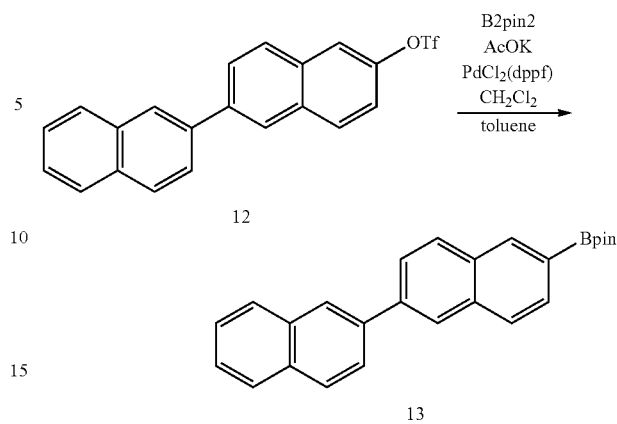

(Step 15) the Synthesis of the Intermediate Compound Represented by the Following Formula 13

Toluene (350 parts), the intermediate compound represented by formula 12 obtained in Step 14 (14.5 parts), bis(pinacolato)diboron (11.0 parts), potassium acetate (7.1 parts), and [1,1'-bis(diphenylphosphino)ferrocene]dichloropalladium(II) dichloromethane adduct (0.9 parts) were mixed and stirred under nitrogen atmosphere at the reflux temperature for 6 hours. The reaction solution obtained was cooled to the room temperature and the solid content was separated by filtration. The filtrate containing the product was obtained. Next, the filtrate was purified by silica gel column chromatography (developing solvent; toluene) and the solvent was distilled off under the reduced pressure to obtain the intermediate compound represented by the following formula 13 (13.5 parts, yield 99%)

(Step 16) the Synthesis of the Aromatic Compound Represented by No. 30 of the Concrete Examples DMF (70 parts), water (5 parts), the compound represented by above formula 1 synthesized by the method according to the description in JP 2009-196975 A (0.7 parts), the intermediate compound represented by formula 13 obtained in Step 15 (0.95 parts), potassium phosphate (0.7 parts), palladium acetate (0.10 parts) and 2-dicycloohexylphosphino-2',6'-dimethoxybiphenyl(SPhos) (0.70 parts) were mixed and stirred under a nitrogen atmosphere at 80° C. for 5 hours. After the reaction solution obtained was cooled to the room temperature, water (300 parts) was added and the solid content was separated out by filtration. After the solid obtained was washed with acetone and DMF and dried, the compound represented by No. 30 of the concrete examples (0.4 parts, yield 41%) was obtained by performing the sublimation to purify.

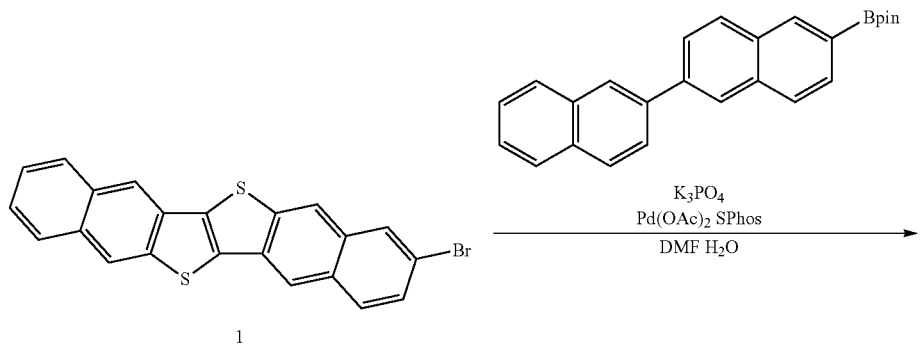

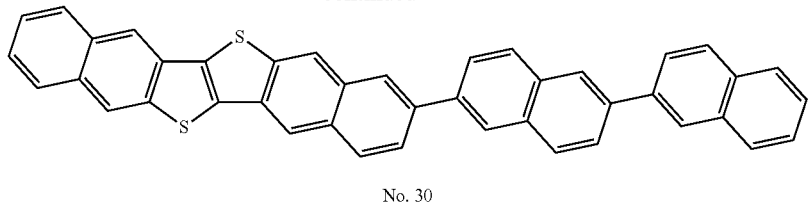

No. 30

The results of the EI-MS spectrum measurement and the thermal analytical measuring of the compound represented by No. 30 of the concrete examples obtained in Example. 11 were as follows.
EI-MS m/z: Calculated for $C_{42}H_{24}S_2[M^+]$: 592.77. Found: 592.45 Thermal analytical measuring (heat absorption peak): 464.0° C. (under nitrogen atmosphere conditions)

Example 12 (Manufacture and Evaluation of Organic Photoelectric Conversion Element 5 of Compound Represented by No. 29 of Concrete Examples Obtained in Example 10)

On the ITO transparent conductive glass (manufactured by GEOMATEC Co., Ltd. the film thickness of ITO 150 nm), the fused polycyclic aromatic compound represented by No. 29 of the concrete examples obtained in Example 10 was formed as the film having a film thickness of 100 nm by the resistant heating type vacuum vapor deposition. Next, the organic photoelectric conversion element 5 of the present invention was manufactured by forming film having a thickness of 100 nm from aluminum as an electrode by the vacuum film deposition. When the voltage of 1 V was applied to the ITO and aluminum as an electrode and the light irradiation was performed with the light having a wavelength of 450 nm, the bright and dark electric current ratio was 210000.

Comparative Example 5 (Manufacture and Evaluation of Organic Photoelectric Conversion Element 6 for Comparison)

The organic photoelectric conversion element 6 for comparison was manufactured by the method according to Example 12 except for that the fused polycyclic aromatic compound represented by No. 29 of the concrete examples obtained in Example 10 was replaced with the compound represented by above formula (DNTT) synthesized according to the description in JP 4958119 B. When the voltage of 1 V was applied to the ITO and aluminum as an electrode and the light irradiation was performed with the light having a wavelength of 450 nm, the bright and dark electric current ratio was 6.

Comparative Example 6 (Manufacture and Evaluation of Organic Photoelectric Conversion Element 7 for Comparison)

The organic photoelectric conversion element 7 for comparison was manufactured by the method according to Example 12 except for that the fused polycyclic aromatic compound represented by No. 29 of the concrete examples obtained in Example 10 was replaced with the compound represented by above formula (R). When the voltage of 1 V was applied to the ITO and aluminum as an electrode and the light irradiation was performed with the light having a wavelength of 450 nm, the bright and dark electric current ratio was 5000.

Example 13 (Manufacture and Evaluation of Organic Photoelectric Conversion Element 8 of Compound Represented by No. 30 of Concrete Examples Obtained in Example 11)

On the ITO transparent conductive glass (manufactured by GEOMATEC Co., Ltd. the film thickness of ITO 150 nm), the fused polycyclic aromatic compound represented by No. 30 of the concrete examples obtained in Example 11 was formed as the film having a film thickness of 100 nm by the resistant heating type vacuum vapor deposition. Next, the organic photoelectric conversion element 8 of the present invention was manufactured by forming film having a thickness of 100 nm from aluminum as an electrode by the vacuum film deposition. When the voltage of 1 V was applied to the ITO and aluminum as an electrode and the light irradiation was performed with the light having a wavelength of 450 nm, the bright and dark electric current ratio was 500000.

Example 14 (Manufacture of Field-Effect Transistor 6 of Present Invention)

On the n-doped silicon wafer with Si thermal oxide film subjected to the surface treatment with 1,1,1,3,3,3-hexamethyldisilazane, the fused polycyclic aromatic compound represented by No. 29 of the concrete examples obtained in Example 10 was formed as the film having a thickness of 100 nm by the resistant heating type vacuum vapor deposition. Next, on the organic thin film obtained above Au was vacuum vapor deposited to manufacture the source electrode and the drain electrode having a channel length of 20 to 200 μm and a channel width of 2000 μm, respectively by using the shadow mask. Therefore, the top contact type field-effect transistor element 6 (FIG. 1B) of the present invention was manufactured. Note that in the field-effect transistor element 6, the thermal oxide film of the n-doped silicon wafer with thermal oxide film has the function of the insulator layer and the n-doped silicon wafer functions as both the substrate and the gate electrode.

Comparative Example 7 (Manufacture of Field-Effect Transistor 7 for Comparison)

The field-effect transistor element 7 for comparison was manufactured by the method according to Example 14 except for that the fused polycyclic aromatic compound represented by No. 29 of the concrete examples obtained in Example 10 was replaced with the compound represented by above formula (R).
On one substrate, four field-effect transistor elements 6 and 7 were manufactured respectively by the method according to Example 14 and Comparative Example 7. After heating the field-effect transistor elements 6 and 7 at 120° C. for 30 minutes under air pressure, the carrier mobility μ was measured by the method aforementioned. Next, after further heating at 150° C. for 30 minutes under air pressure the field-effect transistor elements 6 and 7 subjected to the measurement of the carrier mobility/I after heating at 120° C. aforementioned, the carrier mobility μ was measured by the method aforementioned. Finally, after further heating at 180° C. for 30 minutes under air pressure the field-effect transistor elements 6 and 7 subjected to the measurement of the carrier mobility/I after heating at 150° C. aforementioned, the carrier mobility μ was measured by the same method as the method aforementioned. The heat resistance was evaluated based on the same evaluation criteria as the above. The results were shown in Table 9.

TABLE 9

9 Results of heat resistance test of field-effect transistor (FET) element

| | Heat conditions | | |
|---|---|---|---|
| Element | 120° C. for 30 minutes | 150° C. for 30 minutes | 180° C. for 30 minutes |
| FET element 6 (Example) | A | A | A |
| FET element 7 (Example) | A | A | C |

(Heat Resistance Test of Organic Thin Film)

On the n-doped silicon wafer with Si thermal oxide film subjected to the surface treatment with 1,1,1,3,3,3-hexamethyldisilazane, the fused polycyclic aromatic compound represented by No. 29 of the concrete examples obtained in Example 10 and the compound represented by formula (R) used in Comparative Example 1 were formed as the organic thin film having a thickness of 100 nm by the vapor deposition method described in Example 14 respectively. After heating the organic thin films obtained above at 120° C. for 30 minutes under air pressure, the organic thin films were cooled to the room temperature temporarily. Next, after heating the organic thin films at 150° C. for 30 minutes under air pressure, the organic thin films were cooled to the room temperature temporarily. After heating the organic thin film at 180° C. for 30 minutes under air pressure yet again, the surface roughness (Sa) just after manufacturing the organic thin film, and the surface roughness after heating at 120° C., 150° C., and 180° C. were calculated by using the AFM analysis program. The results were shown in Table 10.

The surface state of the organic thin film for calculating the surface roughness used above was observed by AFM (scanning range: 1 μm) The AFM image of the organic thin film containing the fused polycyclic aromatic compound represented by No. 29 of the concrete examples was shown in FIG. 9 and the AFM image of the organic thin film containing the compound represented by formula (R) was shown in FIG. 10, respectively.

TABLE 10

10 Results of heat resistance test (surface roughness (Sa))

| Compound | Immediately after film formation | 180° C. for 30 minutes |
|---|---|---|
| No. 29 | 2.9 nm | 7.8 nm |
| Formula (R) | 3.0 nm | 72.2 nm |

From the results in Table 9, it is clear that the field-effect transistor of the present invention has more excellent heat resistance than the field-effect transistor for comparison.

In addition, the results in Table 10 reveal that the change of the surface roughness of the organic thin film containing the fused polycyclic aromatic compound represented by No. 29 of the concrete examples before and after heating test is smaller than the organic thin film containing the compound represented by formula (R) for comparison. The comparison of the image observed by AFM shown in FIG. 9 of the organic thin film containing the fused polycyclic aromatic compound represented by No. 29 of the concrete examples and the image observed by AFM shown in FIG. 10 of the organic thin film comprising the compound represented by formula (R) for comparison shows it clearly.

Example 15 and Comparative Example 8 (Heat Resistance Test of Field-Effect Transistor Element 8 and 9)

The heat resistance test of the field-effect transistor elements 8 and 9 manufactured by using the fused polycyclic aromatic compound represented by No 30 of the concrete examples and DNTT aforementioned were performed by the same method as the heat resistance test of the field-effect transistor element manufactured by using the fused polycyclic aromatic compound represented by No 29 of the concrete examples obtained in Example 10 and the compound represented by formula (R). The results were shown in Table 11.

TABLE 11

11 Results of heat resistance test of field-effect transistor (FET) element

| | Heat conditions | | |
|---|---|---|---|
| Element | 120° C. for 30 minutes | 150° C. for 30 minutes | 180° C. for 30 minutes |
| FET element 8 (Example) | A | A | A |
| FET element 9 (Example) | A | A | C |

(Heat Resistance Test of Organic Thin Film)

The heat resistance test of the organic thin film manufactured by using the fused polycyclic aromatic compound represented by No. 30 of the concrete examples obtained in Example 11 was performed by the same method as the heat resistance test of the organic thin film manufactured by using the fused polycyclic aromatic compound represented by No. 29 of the concrete examples obtained in Example 10. The results were shown in Table 12.

The surface state of the organic thin film for calculating the surface roughness used above was observed by AFM (scanning range: 1 μm) The AFM image of the organic thin film containing the fused polycyclic aromatic compound represented by No. 30 of the concrete examples was shown in FIG. 11.

TABLE 12

12 Results of heat resistance test (surface roughness (Sa))

| Compound | Immediately after film formation | 180° C. for 30 minutes |
|---|---|---|
| No. 30 | 3.9 nm | 43.4 nm |

From the results in Table 11, it is clear that the field-effect transistor of the present invention has more excellent heat resistance than the field-effect transistor for comparison.

In addition, the results in Tables 10 and 12 reveal that the change of the surface roughness of the organic thin film containing the fused polycyclic aromatic compound represented by No. 30 of the concrete examples before and after heating test is smaller than the organic thin film containing the compound represented by formula (R) for comparison. The comparison of the image observed by AFM shown in FIG. 11 of the organic thin film containing the fused polycyclic aromatic compound represented by No. 30 of the concrete examples and the image observed by AFM shown in FIG. 10 of the organic thin film containing the compound represented by formula (R) for comparison shows it clearly.

Comparative Example 9 (Synthesis of the Fused Polycyclic Aromatic Compound Represented by Following Formula (R₃))

DMF (50 parts), the compound represented by following formula 14 synthesized by the method according to the description in JP 2009-196975 A (0.5 parts), 4-(p-terphenyl)boronic acid (0.69 parts), tripotassium phosphate (0.85 parts), and tetrakis(triphenylphosphine)palladium(0) (0.04 parts) were mixed and stirred under a nitrogen atmosphere at 80° C. for 6 hours. After the reaction solution obtained was cooled to the room temperature, water (50 parts) was added and the solid content was separated out by filtration. The solid obtained was washed with acetone and DMF and dried to obtain the compound represented by following formula (R3) (0.56 parts, yield 70%). The compound represented by formula (R3) was subjected to the sublimation to purify. As a result, the compound represented by following formula (R3) was thermally decomposed and failed to be purified.

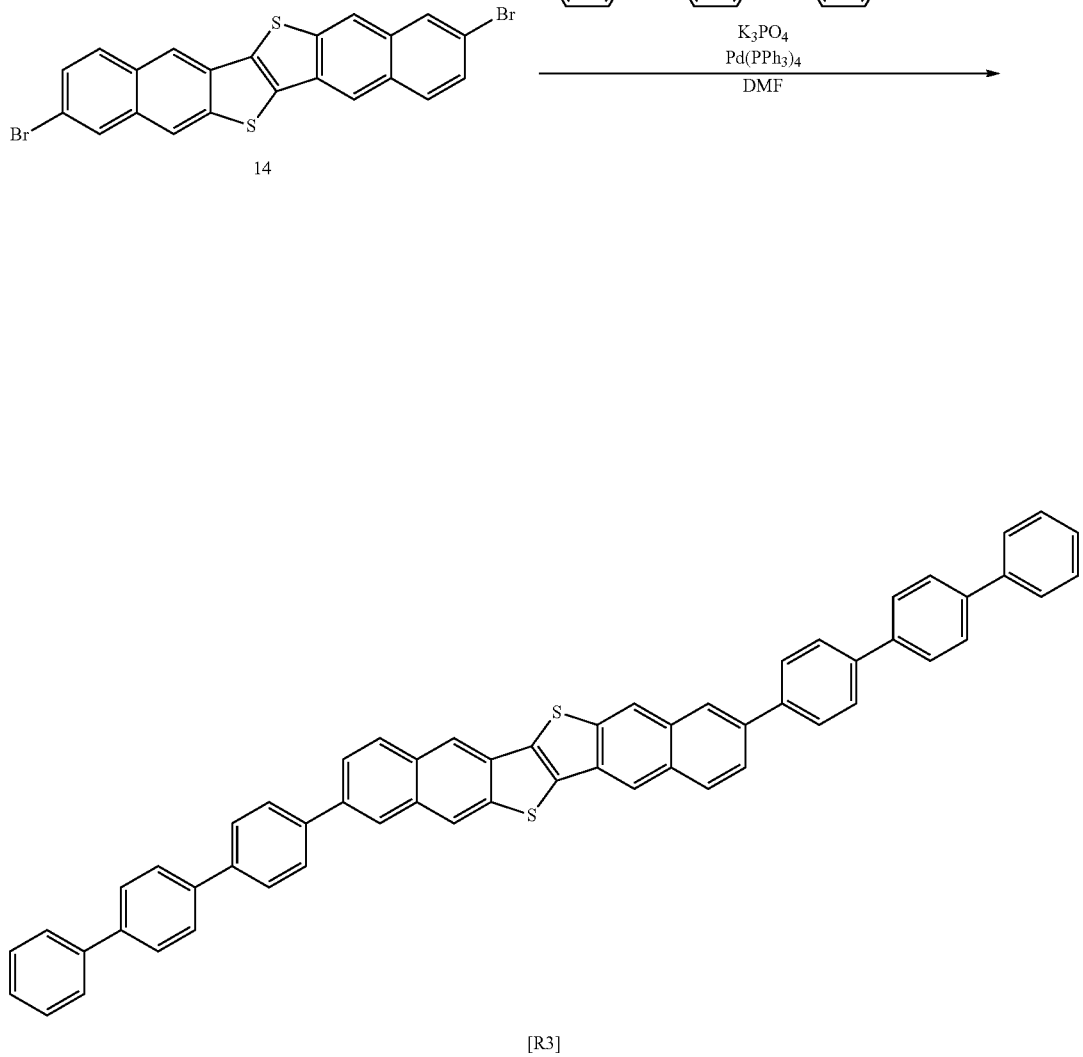

[R3]

Comparative Example 10 (Attempt of Manufacture and Evaluation of Organic Photoelectric Conversion Element 9)

On the ITO transparent conductive glass (manufactured by GEOMATEC Co., Ltd. the film thickness of ITO 150 nm), the fused polycyclic aromatic compound represented by formula (R3) obtained in Comparative Example 9 before the sublimation to purify was attempted to form as a film having a film thickness of 100 nm by the resistant heating type vacuum vapor deposition. As a result, because the thermal decomposition behavior was shown, the organic photoelectric conversion element for comparison could not be manufactured.

INDUSTRIAL APPLICABILITY

According to the present invention, the fused polycyclic aromatic compound having excellent heat resistance in a practical process temperature range; an organic thin film containing said compound; and an organic semiconductor device (field-effect transistor or organic photoelectric conversion element) having said organic thin film can be provided.

The invention claimed is:

1. A fused polycyclic aromatic compound represented by general formula (1):

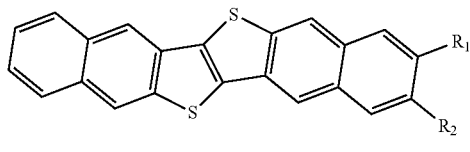
(1)

wherein in formula (1), one of $R_1$ and $R_2$ is represented by general formula (2) which is a substituent having 3 to 5 ring structures,

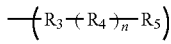
(2)

wherein in formula (2), n represents an integer of 0 to 2, $R_3$ represents a divalent linking group obtained by removing two hydrogen atoms from benzene or naphthalene, $R_4$ represents a divalent linking group obtained by removing two hydrogen atoms from an aromatic ring of an aromatic hydrocarbon, and when n is 2, a plurality of $R_{4s}$ may be the same as or different from each other, $R_5$ represents an aromatic hydrocarbon group, and the other is a hydrogen atom.

2. The fused polycyclic aromatic compound according to claim 1, wherein the substituent represented by formula (2) has 21 to 30 carbon atoms.

3. The fused polycyclic aromatic compound according to claim 1, represented by general formula (3):

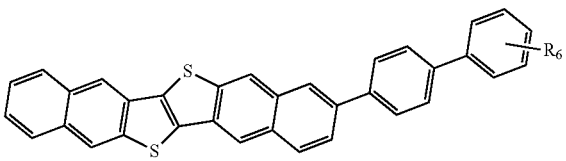
(3)

wherein in formula (3), $R_6$ is represented by general formula (4):

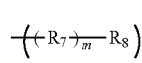
(4)

wherein in formula (4), m represents an integer of 0 or 1, $R_7$ represents a divalent linking group obtained by removing two hydrogen atoms from an aromatic ring of an aromatic hydrocarbon, and $R_8$ represents an aromatic hydrocarbon group.

4. The fused polycyclic aromatic compound according to claim 1, wherein the substituent represented by formula (2) is a phenyl group having an aromatic hydrocarbon group selected from a group consisting of phenylnaphthyl group, terphenyl group, biphenylnaphthyl group, phenanthrene group, anthranil group, naphthylphenyl group, fluorenyl group, and pyrenyl group.

5. The fused polycyclic aromatic compound according to claim 1, represented by general formula (5):

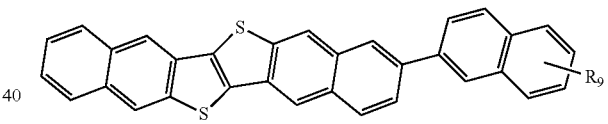
(5)

wherein in formula (5), $R_9$ is represented by general formula (6) which is a substituent having 1 to 3 ring structures:

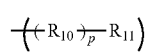
(6)

wherein in formula (6), p represents an integer of 0 to 2, $R_{10}$ represents a divalent linking group obtained by removing two hydrogen atoms from an aromatic ring of an aromatic hydrocarbon, $R_{11}$ represents an aromatic hydrocarbon group.

6. The fused polycyclic aromatic compound according to claim 1, wherein the substituent represented by formula (2) is a naphthyl group having an aromatic hydrocarbon group selected from a group consisting of naphthyl group, biphenyl group, phenylnaphthyl group, terphenyl group, phenanthrene group, anthranil group, naphthylphenyl group, and fluorenyl group.

7. An organic thin film containing the fused polycyclic aromatic compound according to claim 1.

8. A field-effect transistor having the organic thin film according to claim 7.

9. A material for a photoelectric conversion element containing the fused polycyclic aromatic compound according to claim 1.

10. A photoelectric conversion element having the organic thin film according to claim 7.

* * * * *

UNITED STATES PATENT AND TRADEMARK OFFICE
CERTIFICATE OF CORRECTION

PATENT NO. : 12,024,526 B2
APPLICATION NO. : 17/642808
DATED : July 2, 2024
INVENTOR(S) : Yusuke Tone et al.

It is certified that error appears in the above-identified patent and that said Letters Patent is hereby corrected as shown below:

In the Claims

Column 75, Line 58, Claim 1, delete "$R_4s$" and insert -- $R_{4s}$ --

Signed and Sealed this
Seventeenth Day of September, 2024

Katherine Kelly Vidal
*Director of the United States Patent and Trademark Office*